(12) United States Patent
Nobile et al.

(10) Patent No.: US 11,111,531 B2
(45) Date of Patent: *Sep. 7, 2021

(54) ISOTHERMAL METHODS FOR AMPLIFYING NUCLEIC ACID SAMPLES

(71) Applicant: Tangen Biosciences, Inc., Branford, CT (US)

(72) Inventors: John R. Nobile, Guilford, CT (US); John Davidson, Guilford, CT (US)

(73) Assignee: TANGEN BIOSCIENCES, INC., Branford, CT (US)

(*) Notice: Subject to any disclaimer, the term of this patent is extended or adjusted under 35 U.S.C. 154(b) by 53 days.

This patent is subject to a terminal disclaimer.

(21) Appl. No.: 16/509,447

(22) Filed: Jul. 11, 2019

(65) Prior Publication Data

US 2019/0376130 A1    Dec. 12, 2019

Related U.S. Application Data

(63) Continuation of application No. 15/326,604, filed as application No. PCT/US2015/040792 on Jul. 16, 2015, now Pat. No. 10,364,458.

(60) Provisional application No. 62/025,345, filed on Jul. 16, 2014.

(51) Int. Cl.
  *C12Q 1/6858* (2018.01)
  *B01L 7/00* (2006.01)

(52) U.S. Cl.
  CPC .............. *C12Q 1/6858* (2013.01); *B01L 7/52* (2013.01); *B01L 7/525* (2013.01)

(58) Field of Classification Search
  CPC ............ C12Q 2525/155; C12Q 1/6858; C12Q 2531/119; C12Q 2535/125
  See application file for complete search history.

(56) References Cited

U.S. PATENT DOCUMENTS

| | | |
|---|---|---|
| 4,656,134 A | 4/1987 | Ringold |
| 4,683,195 A | 7/1987 | Mullis et al. |
| 4,683,202 A | 7/1987 | Mullis |
| 4,766,067 A | 8/1988 | Biswas |
| 4,795,699 A | 1/1989 | Tabor et al. |
| 4,800,159 A | 1/1989 | Mullis et al. |
| 4,889,818 A | 12/1989 | Gelfand et al. |
| 4,921,794 A | 5/1990 | Tabor et al. |
| 4,965,188 A | 10/1990 | Mullis et al. |
| 4,994,370 A | 2/1991 | Silver et al. |
| 5,066,584 A | 11/1991 | Gyllensten et al. |
| 5,091,310 A | 2/1992 | Innis |
| 5,102,784 A | 4/1992 | George, Jr. |
| 5,122,464 A | 6/1992 | Wilson et al. |
| 5,130,238 A | 7/1992 | Malek et al. |
| 5,142,033 A | 8/1992 | Innis |
| 5,399,491 A | 3/1995 | Kacian et al. |
| 5,409,818 A | 4/1995 | Davey et al. |
| 5,455,166 A | 10/1995 | Walker |
| 5,648,211 A | 7/1997 | Fraiser et al. |
| 6,410,278 B1 | 6/2002 | Notomi et al. |
| 6,743,605 B1 | 6/2004 | Rabbani et al. |
| 7,056,671 B2 | 6/2006 | Enoki et al. |
| 8,460,874 B2 | 6/2013 | Peleg |
| 9,200,317 B2 | 12/2015 | Tisi et al. |
| 2004/0146933 A1 | 7/2004 | Quinn et al. |
| 2009/0142771 A1 | 6/2009 | Breidenthal et al. |
| 2010/0056383 A1* | 3/2010 | Ririe .................. B01L 3/50273 506/7 |
| 2010/0273219 A1 | 10/2010 | May et al. |
| 2011/0097764 A1* | 4/2011 | Johnson .................. C12P 19/34 435/91.21 |
| 2012/0157326 A1 | 6/2012 | Tisi et al. |
| 2012/0244534 A1 | 9/2012 | Ching et al. |

FOREIGN PATENT DOCUMENTS

| | | |
|---|---|---|
| CN | 102639712 A | 8/2012 |
| CN | 102439177 B | 10/2014 |
| CN | 102652176 B | 9/2016 |
| EP | 0497272 A1 | 8/1992 |
| WO | 9601327 A1 | 1/1996 |
| WO | 9704126 A1 | 2/1997 |
| WO | 0028082 A1 | 5/2000 |
| WO | 0134790 A1 | 5/2001 |
| WO | 0224902 A1 | 3/2002 |
| WO | 03016569 A1 | 2/2003 |
| WO | 03072805 A2 | 9/2003 |
| WO | 2004027025 A2 | 4/2004 |
| WO | 2004062338 A2 | 7/2004 |

(Continued)

OTHER PUBLICATIONS

European Examination Report dated Feb. 28, 2020 to EP Patent Application No. 15821916.2.
Extended European Search Report dated Dec. 4, 2017, to EP Patent Application No. 15821916.2.
First Office action dated Sep. 27, 2019 to CN Patent Application No. 201580038542.0.
Non-Final Office Action dated Oct. 17, 2018, to U.S. Appl. No. 15/326,604.
Notice of Allowance dated Jun. 10, 2019, to U.S. Appl. No. 15/326,604.
Atschul, S. F. et al., J. Molec. Biol. 215:403-410 (1990).
Barany, F. 1991. Proc. Natl. Acad. Sci. USA 88, 189-193.
Barringer, K. Barringer, et al. 1990. Gene 89, 117-122.

(Continued)

*Primary Examiner* — Cynthia B Wilder
(74) *Attorney, Agent, or Firm* — Spectrum IP Law Group LLC

(57) ABSTRACT

The description provides two-stage methods of nucleic acid amplification and detection reactions, which are useful for rapid pathogen detection or disease diagnosis. In particular, the description provides a method comprising a first-stage slow rate amplification reaction followed by a plurality of second-stage fast rate amplification reactions that are simultaneously monitored in real-time, and wherein a rapid rate of amplification is indicative of the presence of a site of interest.

24 Claims, 8 Drawing Sheets

(56) References Cited

FOREIGN PATENT DOCUMENTS

| WO | 2006010948 A1 | 2/2006 |
| WO | 2009004630 A1 | 1/2009 |
| WO | 2010007355 A1 | 1/2010 |
| WO | 2013177429 A2 | 11/2013 |
| WO | 2014153071 A1 | 9/2014 |

OTHER PUBLICATIONS

Curtis KA, Rudolph DL, Owen SM (2008). "Rapid detection of HIV-1 by reverse-transcription, loop-mediated isothermal amplification (RT-LAMP)". J. Virol. Methods 151 (2): 264-70. doi:10.1016/j.jviromet.2008.04.011. PMID 18524393.
Devereux, J., et al., Nucleic Acids Research 12(1): 387 (1984).
Francois P, Tangomo M, Hibbs J, Bonetti EJ, Boehme CC, Notomi T, Perkins MD, Schrenzel J (2011). "Robustness of a loop-mediated isothermal amplification reaction for diagnostic applications". FEMS Immunol. Med. Microbiol. 62 (1): 41-8. doi:10.1111/j.1574-695X.2011.00785.x. PMID 21276085.
Gandelman et al., Loop-Mediated Amplification Accelerated by Stem Primers. Int. J. Mol. Sci. 2011; 12(12):9108-9124.
Geojith G, Dhanasekaran S, Chandran SP, Kenneth J (2011). "Efficacy of loop mediated isothermal amplification (LAMP) assay for the laboratory identification of *Mycobacterium tuberculosis* isolates in a resource limited setting". J. Microbiol. Methods 84 (1): 71-3. doi:10.1016/j.mimet.2010.10.015. PMID 21047534.
Gill, Pooria, et al.; Nucleosides, Nucleotides and Nucleic Acids, 2008. v27(3):224-243.
Guatelli, J. C. Guatelli, et al. 1990. Proc. Natl. Acad. Sci. USA 87, 1874-1878.
Hefner G. J., Yang I. C., Wolter L. C., Stafford M. R., Giffard P. M, BioTechniques, 2001, vol. 30, No. 4, pp. 852-867.
International Search Report and Written Opinion dated Oct. 23, 2015, for PCT/US2015/040792 as filed on Jul. 16, 2015.
Iseki H, Alhassan A, Ohta N, Thekisoe OM, Yokoyama N, Inoue N, Nambota A, Yasuda J, Igarashi I (2007). "Development of a multiplex loop-mediated isothermal amplification (mLAMP) method for the simultaneous detection of bovine Babesia parasites". J. Microbiol. Methods 71 (3): 281-7. doi:10.1016/j.mimet.2007.09.019. PMID 18029039.
Kwoh, D. Y., et at. 1989. Proc. Natl. Acad Sci. USA 86, 1173-1177.
Lizardi, P. M. Lizardi, et al. 1988. BioTechnology 6, 1197-1202.
Lizardi, Paul M. et al., Nature Genetics, 19, 225-232, Jul. 1998.
Macarthur G (2009). Global health diagnostics: research, development and regulation. Academy of Medical Sciences Workshop Report (PDF). Academy of Medical Sciences (Great Britain). ISBN 978-1-903401-20-0.
Mori Y, Kitao M, Tomita N, Notomi T (2004). "Real-time turbidimetry of LAMP reaction for quantifying template DNA". J. Biochem. Biophys. Methods 59 (2): 145-57. doi:10.1016/j.jbbm.2003.12.005. PMID 15163526.
Mori Y, Nagamine K, Tomita N, Notomi T (2001). "Detection of loop-mediated isothermal amplification reaction by turbidity derived from magnesium pyrophosphate formation". Biochem. Biophys. Res. Commun. 289 (1): 150-4. doi:10.1006/bbrc.2001.5921. PMID 11708792.
Nagamine K, Hase T, Notomi T (2002). "Accelerated reaction by loop-mediated isothermal amplification using loop primers". Mol. Cell. Probes 16 (3): 223-9. doi:10.1006/mcpr.2002.0415. PMID 12144774.
Njiru ZK, Mikosza AS, Armstrong T, Enyaru JC, Ndung'u JM, Thompson AR (2008). "Loop-mediated isothermal amplification (LAMP) method for rapid detection of Trypanosoma brucei rhodesiense". PLoS Negl Trop Dis 2 (1): e147. doi:10.1371/journal.pntd.0000147. PMC 2238707. PMID 18253475. open access publication—free to read.
Njiru ZK, Mikosza AS, Matovu E, Enyaru JC, Ouma JO, Kibona SN, Thompson RC, Ndung'u JM (2008). "African trypanosomiasis: sensitive and rapid detection of the sub-genus *Trypanozoon* by loop-mediated isothermal amplification (LAMP) of parasite DNA". Int. J. Parasitol. 38 (5): 589-99. doi:10.1016/j.ijpara.2007.09.006. PMID 17991469.
Notomi T, Okayama H, Masubuchi H, Yonekawa T, Watanabe K, Amino N, Hase T (2000). "Loop-mediated isothermal amplification of DNA". Nucleic Acids Res. 28 (12): E63. doi: 0.1093/nar/28.12.e63. PMC 102748. PMID 10871386.
Poon LL, Wong BW, Ma EH, Chan KH, Chow LM, Abeyewickreme W, Tangpukdee N, Yuen KY, Guan Y, Looareesuwan S, Peiris JS (2006). "Sensitive and inexpensive molecular test for falciparum malaria: detecting Plasmodium falciparum DNA directly from heat-treated blood by loop-mediated isothermal amplification". Clin. Chem. 52 (2): 303-6. doi:10.1373/clinchem.2005.057901. PMID 16339303.
Saiki, R. K. Saiki, et al. 1985. Science 230, 1350-1354.
Sattabongkot J, Tsuboi T, Han ET, Bantuchai S, Buates S (2014). "Loop-mediated isothermal amplification assay for rapid diagnosis of malaria infections in an area of endemicity in Thailand". J. Clin. Microbiol. 52 (5): 1471-7. doi:10.1128/JCM.03313-13. PMID 24574279.
Tanner NA, Zhang Y, Evans TC (2012). "Simultaneous multiple target detection in real-time loop-mediated isothermal amplification". BioTechniques 53 (2): 81-9. doi:10.2144/0000113902. PMID 23030060.
Tomita N, Mori Y, Kanda H, Notomi T (2008). "Loop-mediated isothermal amplification (LAMP) of gene sequences and simple visual detection of products". Nat Protoc 3 (5): 877-82. doi:10.1038/nprot.2008.57. PMID 18451795.
Torres C, Vitalis EA, Baker BR, Gardner SN, Torres MW, Dzenitis JM (2011). "LAVA: an open-source approach to designing LAMP (loop-mediated isothermal amplification) DNA signatures". BMC Bioinformatics 12: 240. doi:10.1186/1471-2105-12-240. PMC 3213686. PMID 21679460. open access publication—free to read.
Walker, G. T. Walker, et al. 1992. Nuc. Acids. Res. 20, 1691-1696.
Walker, G. T. Walker, et at. 1992. Proc. Natl. Acad. Sci. USA 89, 392-396.
Wu, D. Y., et al. 1989. Genomics 4, 560-569.
Extended European Search Report dated Sep. 7, 2020, to EP Patent Application No. 15821916.2.
Second Office Action dated Mar. 16, 2020 to CN Patent Application No. 201580038542.0.

* cited by examiner

ISOTHERMAL METHODS FOR AMPLIFYING NUCLEIC ACID SAMPLES

CROSS-REFERENCE TO RELATED APPLICATIONS

This application is a continuation and claims priority under 35 U.S.C. § 120 of pending U.S. patent application Ser. No. 15/326,604, filed Jan. 16, 2017, entitled "Isothermal Methods For Amplifying Nucleic Acid Samples which in turn is a U.S. National Entry of International Application No. PCT/US2015/040792, titled, "Isothermal Methods For Amplifying Nucleic Acid Samples", as filed on Jul. 16, 2015, and also claims the benefit of, and priority to, U.S. Provisional Application Ser. No. 62/025,345 filed Jul. 16, 2014, entitled "Isothermal Methods for Amplifying Nucleic Acid Samples", which are incorporated herein by reference in their entirety.

BACKGROUND

1. Field of the Discovery

The description provides methods of nucleic acid amplification and detection reactions, which are useful for rapid pathogen detection or disease diagnosis.

2. Background Information

Nucleic acid analysis methods based on the complementarity of nucleic acid nucleotide sequences can analyze genetic traits directly. Accordingly, these methods are a very powerful means for identification of genetic diseases, cancer, microorganisms etc. Nevertheless, the detection of a target gene or nucleic acid present in a very small amount in a sample is not easy, and therefore, amplification of the target gene or its detection signal is necessary. As such, in vitro nucleic acid amplification technologies (NAATs) are an invaluable and powerful tool for detection and analysis of small amounts of nucleic acid in many areas of research and diagnosis.

NAAT techniques allow detection and quantification of a nucleic acid in a sample with high sensitivity and specificity. NAAT techniques may be used to determine the presence of a particular template nucleic acid in a sample, as indicated by the presence of an amplification product (i.e., amplicon) following the implementation of a particular NAAT. Conversely, the absence of any amplification product indicates the absence of template nucleic acid in the sample. Such techniques are of great importance in diagnostic applications, for example, for determining whether a pathogen is present in a sample. Thus, NAAT techniques are useful for detection and quantification of specific nucleic acids for diagnosis of infectious and genetic diseases.

NAATs can be grouped according to the temperature requirements of the procedure. For example, the polymerase chain reaction (PCR) is the most popular method as a technique of amplifying nucleic acid in vitro. This method was established firmly as an excellent detection method by virtue of high sensitivity based on the effect of exponential amplification. Further, since the amplification product can be recovered as DNA, this method is applied widely as an important tool supporting genetic engineering techniques such as gene cloning and structural determination. In the PCR method, however, temperature cycling or a special temperature controller is necessary for practice; the exponential progress of the amplification reaction causes a problem in quantification; and samples and reaction solutions are easily contaminated from the outside to permit nucleic acid mixed in error to function as a template (See R. K. Saiki, et al. 1985. *Science* 230, 1350-1354). Other PCR-based amplification techniques, for example, transcription-based amplification (D. Y. Kwoh, et at. 1989. *Proc. Natl. Acad Sci*. USA 86, 1173-1177), ligase chain reaction (LCR; D. Y. Wu, et al. 1989. *Genomics* 4, 560-569; K. Barringer, et al. 1990. *Gene* 89, 117-122; F. Barany. 1991. *Proc. Natl. Acad. Sci*. USA 88, 189-193), and restriction amplification (U.S. Pat. No. 5,102,784) similarly require temperature cycling.

More recently, a number of isothermal nucleic acid amplification techniques (iNAATs) have been developed. That is, these techniques do not rely on thermocycling to drive the amplification reaction. Isothermal amplification techniques typically utilize DNA polymerases with strand-displacement activity, thus eliminating the high temperature melt cycle that is required for PCR. This allows isothermal techniques to be faster and more energy efficient than PCR, and also allows for more simple and thus lower cost instrumentation since rapid temperature cycling is not required. For example, methods such as Strand Displacement Amplification (SDA; G. T. Walker, et at. 1992. *Proc. Natl. Acad. Sci*. USA 89, 392-396; G. T. Walker, et al. 1992. *Nuc. Acids. Res.* 20, 1691-1696; U.S. Pat. No. 5,648,211 and EP 0 497 272, all disclosures being incorporated herein by reference); self-sustained sequence replication (3SR; J. C. Guatelli, et al. 1990. *Proc. Natl. Acad. Sci*. USA 87, 1874-1878, which is incorporated herein by reference); and Qβ replicase system (P. M. Lizardi, et al. 1988. *BioTechnology* 6, 1197-1202, which is incorporated herein by reference) are isothermal reactions (See also, Nucleic Acid Isothermal Amplification Technologies—A Review. *Nucleosides, Nucleotides and Nucleic Acids,* 2008. v27(3):224-243, which is incorporated herein by reference).

In the SDA method, a special DNA polymerase is used to synthesize a complementary chain starting from an amplification primer complementary to the 3'-side of a certain nucleotide sequence template, and including one or more bumper primers upstream of the amplification primer to displace the double-stranded chain if any at the 5'-side of the sequence template. Because a double-stranded chain at the 5'-side is displaced by a newly synthesized complementary chain, this technique is called the SDA method. The temperature-changing step essential in the PCR method can be eliminated in the SDA method by previously inserting a-restriction enzyme recognition sequence into an annealed sequence as a primer. That is, a nick generated by a restriction enzyme gives a 3'-OH group acting as the origin of synthesis of complementary chain, and the previously synthesized complementary chain is released as a single-stranded chain by strand displacement synthesis and then utilized again as a template for subsequent synthesis of complementary chain. In this manner, the complicated control of temperature essential in the PCR method is not required in the SDA method.

In the SDA method, however, the restriction enzyme generating a nick should be used in addition to the strand displacement-type DNA polymerase. This requirement for the additional enzyme is a major cause for higher cost. Further, because the restriction enzyme is to be used not for cleavage of both double-stranded chains but for introduction of a nick (that is, cleavage of only one of the chains), a dNTP derivative such as alpha-thio dNTP should be used as a substrate for synthesis to render the other chain resistant to digestion with the enzyme. Accordingly, the amplification product by SDA has a different structure from that of natural nucleic acid, and there is a limit to cleavage with restriction enzymes or application of the amplification product to gene cloning. In this respect too, there is a major cause for higher cost. In addition, when the SDA method is applied to an unknown sequence, there is the possibility that the same nucleotide sequence as the restriction enzyme recognition sequence used for introducing a nick may be present in a region to be synthesized. In this case, it is possible that a complete complementary chain is prevented from being synthesized.

Loop-Mediated Isothermal Amplification (LAMP) is another isothermal nucleic acid amplification technique. In LAMP, the target sequence is amplified at a constant temperature of 60-65° C. using either two or three primer sets, and a polymerase with high strand displacement activity in addition to a replication activity. (See Nagamine K, Hase T, Notomi T (2002). "Accelerated reaction by loop-mediated isothermal amplification using loop primers". *Mol. Cell. Probes* 16 (3): 223-9; and U.S. Pat. No. 6,410,278, which is incorporated herein by reference).

LAMP was originally invented and formulated as an isothermal amplification with the strict requirement for four primers: two loop-generating primers (FIP and BIP comprising F1, F2 and B1, B2 priming sites, correspondingly) and two "Displacement primers" (F3 and B3) (FIG. 1). However, in this manifestation the LAMP technology was far too slow for the majority of practical applications. In order to increase the speed of LAMP-based assays the inventors of LAMP came up with additional "Loop primers" which, when added in conjunction with the other primers used in LAMP, resulted in significantly faster assays. Currently, the commonly used manifestation of LAMP requires a total of six primers: two loop-generating primers, two displacement primers and two "Loop primers" ($L_B$ and $L_F$).

Due to the specific nature of the action of these primers, the amount of DNA produced in LAMP is considerably higher than PCR based amplification. The reaction can be followed in real-time either by measuring the turbidity or by fluorescence using intercalating dyes. Dye molecules intercalate or directly label the DNA, and in turn can be correlated to the number of copies initially present. Hence, LAMP can also be quantitative. Thus, LAMP provides major advantages due to its simplicity, ruggedness, and low cost, and has the potential to be used as a simple screening assay in the field or at the point of care by clinicians.

Primer design for LAMP assays thus requires the selection of eight separate regions of a target nucleic acid sequence (the FIP and BIP primers encompass two primer binding sites each), with the BIP/FIP and Loop primers having significant restrictions on their positioning respective to each other. "Loop primers" must be positioned strictly between the B2 and B1 sites and the F2 and F1 sites, respectively, and must be orientated in one particular direction. Further, significant care must be taken in primer design to avoid primer-dimers between the six primers needed (especially difficult as the FIP and BIP primers are generally greater than 40 nucleotides long). As a consequence, LAMP primer design is extremely challenging, especially when targeting highly polymorphic markers and sequences containing complex secondary structure. Also, because LAMP uses 4 (or 6) primers targeting 6 (or 8) regions within a fairly small segment of the genome, and because primer design is subject to numerous constraints, it is difficult to design primer sets for LAMP "by eye". Software is generally used to assist with LAMP primer design, although the primer design constraints mean there is less freedom to choose the target site than with PCR. In a diagnostic application, this must be balanced against the need to choose an appropriate target (e.g., a conserved site in a highly variable viral genome, or a target that is specific for a particular strain of pathogen).

LAMP has been observed to be less sensitive than PCR to inhibitors in complex samples such as blood, likely due to use of a different DNA polymerase (typically Bst DNA polymerase rather than Taq polymerase as in PCR). LAMP is useful primarily as a diagnostic or detection technique, but is not useful for cloning or myriad other molecular biology applications enabled by PCR.

Also, multiplexing approaches for LAMP are relatively undeveloped. The larger number of primers per target in LAMP increases the likelihood of primer-primer interactions for multiplexed target sets. The product of LAMP is a series of concatemers of the target region, giving rise to a characteristic "ladder" or banding pattern on a gel, rather than a single band as with PCR. Although this is not a problem when detecting single targets with LAMP, "traditional" (endpoint) multiplex PCR applications wherein identity of a target is confirmed by size of a band on a gel are not feasible with LAMP. Multiplexing in LAMP has been achieved by choosing a target region with a restriction site, and digesting prior to running on a gel, such that each product gives rise to a distinct size of fragment, although this approach adds complexity to the experimental design and protocol. The use of a strand-displacing DNA polymerase in LAMP also precludes the use of hydrolysis probes, e.g. TaqMan probes, which rely upon the 5'-3' exonuclease activity of Taq polymerase.

More recently, investigators have developed a modified LAMP technique called, STEM. The LAMP-STEM system utilizes "Stem primers," which are directed to the stem portion of the LAMP amplicon (or "dumbbell"). Stem primers can be used as an alternative to LAMP "Loop primers" (See FIG. 2). When used in addition to loop-generating and displacement primers, Stem primers offer similar benefits in speed and sensitivity to the Loop primers. (See Gandelman et al., Loop-Mediated Amplificaiton Accelerated by Stem Primers. Int. J. Mol. Sci. 2011, v12:9108-9124, and US 2012/0157326, which are both incorporated herein by reference). This beneficial effect of Stem primers is surprising as they do not bind to the single-stranded DNA loops, which define the very nature of the LAMP technology. Stem primers can be employed in either orientation, do not require either the B2/B1 or F2/F1 sites to be a specific distance apart, can be multiplexed, and allow the F1 and B1 sites to be positioned further from each other than in LAMP.

STEM primers significantly accelerate LAMP comprised of loop-generating and displacement primers only. They can be used on their own or synergistically with other STEM primers or even Loop primers. Addition of Stem primers into LAMP has a positive effect on both speed and sensitivity. In some cases they improve reproducibility at low copy number. The action of Stem primers can be rationalized via the proposed mechanism of LAMP. They anneal to transiently single-stranded regions of the amplicon and recopy the entire binding sites for the BIP/FIP primers. An additional unique feature is the extra strong intra-molecular self-priming when Stem primers delimit amplicon.

In general, positioning of Stem primers is less constrained than that of Loop primers. A rather challenging primer design involving selection of at least eight binding sites is thus simplified. Furthermore, Stem primers impose fewer limitations on the primer design in terms of stem length, orientation and distances between B1-B2 and F1-F2 sites. In contradiction to the postulated LAMP mechanism that relies on the involvement of displacement primers Stem primers can occasionally allow displacement primers not to be used at all, though it is not clear why this is so. This has a major implication for primer design, as it allows the ability to omit one displacement primer or even both, if necessary.

In many circumstances, such as point of care diagnostics, it is advantageous to be able to simultaneously amplify and detect multiple targets in a single sample using a single assay. This is typically done by combining the amplification of multiple targets in the same tube using different dyes attached to each different target primer set or probe. This very common method has two significant drawbacks. One, since all the primers are together in one solution, there is a very high chance of them cross-reacting with each other and creating dimers and other spurious products that would interfere with the results. This is overcome by laboriously screening many combinations of primer sets to find ones that to not cross-react.

The second major limitation of this method is that there are a limited number of dyes that can be separately detected when in the same solution. Since the wavelength of the emitted light from the dye has some bandwidth to it, each dye's emission spectrum must be adequately separated from the others in order for specific and reliable detection. In practice, this limits each amplification reaction to the detection of 5 or 6 different targets.

A technique that could detect a higher number of targets from the same sample without compromising sensitivity would be a huge improvement for many applications, such as a respiratory infection screening panel, where about 20 different targets are required for a thorough test. Another example is Tuberculosis, where about 20 different alleles must be screened in order to accurately and specifically determine the presence of resistance to either a the two front-line drugs.

SUMMARY

The present description provides an improved nucleic acid amplification technique (NAAT), which is robust, cost-effective, provides for flexibility in primer placement and design, and also demonstrates increased rate, sensitivity, and reproducibility at low copy number. The methods as described herein are advantageous for detecting, in real-time, a nucleic acid region of interest, e.g., for the diagnosis of a disease or infection.

The methods as described herein provide for a first-stage, slow-rate isothermal pre-amplification followed by multiple, discrete second-stage amplification and detection reactions performed in parallel directly on the products from the first-stage primary amplicon amplification product. At least one of the second-stage reactions includes a site or sequence-specific secondary primer ("site-specific primer"), wherein if the template comprises a complementary site for the site-specific primer, the site-specific primer amplification reaction proceeds at a faster rate relative to both the first-stage reaction and second-stage reaction in which no secondary primer is added. In certain embodiments, at least one of the second-stage reactions includes a secondary primer having a base pair mismatch ("mismatch primer"), e.g., 3' mismatch nucleotide ("3' mismatch primer"), wherein the site-specific primer amplification reaction proceeds at a faster rate relative to the first-stage reaction, second-stage reactions in which no secondary primer is added, and the second-stage mismatch primer reaction.

For example, a first-stage region-specific pre-amplification step is done then the reaction is split into multiple reaction chambers, where in each chamber a different set of secondary primers, e.g., loop or stem primers, are introduced that are site-specific sensitive by virtue of, e.g., a 3' end match/mismatch, or annealing temperature difference, so that a much higher speed exponential reaction only occurs if the secondary primers are correctly matched to the sample sequence. The significant difference in amplification rate can be detected by real-time fluorescent measurement of, e.g., an intercalating dye, and thus multiple site-specific reactions within the same region of interest can be individually identified with a single assay.

Thus, in one aspect, the description provides two-stage nucleic acid amplification reaction comprising: providing a target nucleic acid template and at least one primer that anneals to the target nucleic acid template near a region of interest to be amplified; performing a first-stage nucleic acid amplification (or "pre-amp") reaction to amplify the region of interest (amplicon). In certain embodiments, a forward and reverse primer are provided and used to synthesize and amplify the region of interest or amplicon of interest.

Subsequently, the pre-amp reaction product ("amplified region of interest") is utilized in one or more second-stage amplification reactions wherein at leaset one of the reactions includes a site-specific secondary primer, such that rapid amplification occurs only if a complementary sequence for the site-specific primer (i.e., a site-specific region of interest) exists in the amplified region of interest from stage-one (i.e., the nucleic acid region of interest from stage-one is positive for the site of interest). As described herein, the appearance of amplification products in each second-stage reaction can be detected and compared simultaneously and in real-time, wherein a fast rate of amplification relative to the first-stage reaction, a second-stage reaction in which no secondary primer is added, and a second-stage mismatch primer reaction is indicative of the presence of the site-specific region of interest.

In certain embodiments, the site-specific primer comprises a nucleotide mismatch at a site other than the 3' terminus.

In certain embodiments, multiple second-stage nucleic acid amplification reactions are performed in parallel. In a preferred embodiment, the site-specific primer reaction is performed and monitored in parallel with a separate reaction in which similar site-specific primers are used but that comprise a mismatch in its nucleic acid sequence.

In another aspect, a method is described comprising performing multiple, separate or discrete second-stage amplification reactions utilizing the first-stage amplification product or primary amplicon in which the rate of the second-stage amplification reaction is detected and compared as between at least one reaction having a site-specific primer complementary to a site or sequence of interest on the primary amplicon template, and a reaction having a secondary primer that anneals to the same site but comprises a base-pair mismatch (herein, "a mismatch primer"), wherein a faster reaction rate relative to the other is indicative of the presence or absence of the specific site or region of interest. In still additional embodiments, the rate of the second-stage amplification reaction is detected and compared as between at least one reaction having a site-specific primer complementary to a site or sequence of interest on the primary amplicon template, a reaction having a mismatch primer, and a reaction that has no secondary primer, wherein a faster reaction rate relative to the other reactions is indicative of the presence or absence of the specific site or region of interest.

In certain embodiments, the mismatch primer is a mismatch Stem primer. In any of the embodiments described herein, the mismatch primer comprises at least one mismatched nucleotide (i.e., a nucleotide that is not complementary to the template). In certain embodiments, the mismatched nucleotide is at the 3' end of the mismatch primer ("3' mismatch primer").

In certain embodiments, the site-specific primer and the mismatch primer comprise at their 3' ends a nucleotide that is specific or complementary for a multi-allelic or polymorphic site such that, depending on which allele or polymorphism the nucleic acid template comprises, the site-specific primer could comprise a 3' end nucleotide mismatch, and the mismatch primer could contain the 3' end complementary nucleotide. In other words, in certain embodiments, the method comprises performing a plurality of second-stage amplification reactions, wherein each reaction comprises a site-specific primer. However, as described herein, only those amplification reactions comprising a primer that is complementary at its 3' end to the site of interest will proceed at an increased rate relative to the first-stage reaction, and relative to the second-stage reaction comprising a 3' mismatch.

In certain embodiments, the method comprises performing a plurality of second-stage amplification reactions, wherein each respective reaction comprises a site-specific primer. In certain embodiments, the site-specific primer is specific for a different multi-allelic or polymporphic site. In such a configuration, the methods provide for a multiplexing method of determining the presence or absence of multiple polymorphisms simultaneously.

In certain embodiments, the method includes performing at least one additional second-stage amplification reaction in parallel in which no additional primers are added, and monitoring and comparing in real-time the rate of the second-stage amplification reaction as between the reaction comprising the site-specific primer, the reaction comprising the mismatch primer, and the reaction comprising no primer, wherein an enhanced reaction rate relative to the others is indicative of the presence of the specific site or region of interest.

In certain embodiments, the method comprises performing a plurality of separate or discrete second-stage amplification reactions approximately simultaneously. In certain additional embodiments, the discrete reactions comprise the same or different site-specific primers. In certain embodiments, the discrete reactions comprise a plurality or combination of site-specific primers (i.e., "multiplexing reaction").

Although several of the aspects and embodiments refer to a two-staged amplification scheme, the invention is not so limited. Indeed, the methods described herein are predicated upon the surprising discovery that the presence of a specific site or sequence of interest in a target nucleic acid region can be detected by the enhanced rate of amplification with a site-specific or sequence-specific (i.e., complementary) primer relative to the slower rate of an amplification reaction with mismatch primer that, but-for the mismatched base, anneals to the same target region. As such, any number of additional amplification steps can be performed, e.g., 3, 4, 5, 6, 7, 8, 9, etc., and therefore, any number of sites, regions or sequences of interest can be detected. Similarly, for each of the respective site-specific primer reactions to be performed, a parallel mismatch primer reaction can be performed and the rate of amplification of the two reactions monitored.

In any of the aspects or embodiments described herein, the first-stage amplification reaction can comprise site-specific primers such that the first-stage pre-amplification reaction is selective for a particular site of interest, and only if that site or region exists in the sample will rapid amplification of the template proceed at the second or later stage amplification reaction.

In any of the aspects or embodiments described herein, the second-stage (or later stage) amplification reaction can comprise multiple site-specific primers (i.e., "multiplex reaction"). By using differentially labeled site-specific oligonucleotides different amplification products can be detected and compared (i.e., multiplexed) within the same reaction.

In another aspect, the description provides a method for detecting and comparing nucleic acid amplification comprising providing a first reaction chamber; performing a first-stage pre-amplification reaction as described herein in the first reaction chamber; introducing an amount or volume of the first-stage pre-amp reaction directly into a plurality of second reaction chambers, wherein at least one second reaction chamber comprises a site-specific primer, and at least one second reaction chamber comprises a mismatched primer; and performing in each second reaction chamber a second-stage amplification reaction as descried herein; and detecting and comparing the rate of amplification of each reaction simultaneously, wherein a faster rate of amplification in the site-specific primer reaction versus the mismatch primer reaction is indicative of the presence of the site of interest.

In any of the embodiments described herein, the amplification reactions of stage-one and stage-two are performed sequentially in the same reaction container or chamber. In certain embodiments, the amplification reactions are performed sequentially but in different reaction containers or chambers. In a preferred embodiment, the second-stage reaction is performed in parallel in a plurality of containers or chambers, and detected and compared.

In any of the embodiments described herein, the target nucleic acid template is comprised in a suitable buffer and introduced into a container comprising loop-forming primers. In still additional embodiments, the mixture from the first-stage amplification reaction is introduced into a container comprising site-specific or mismatch primers.

In additional embodiments, the first-stage amplification reaction is performed in a container or chamber comprising a channel that is in fluid communication with one or more additional containers or chambers comprising primers for performing the second-stage amplification reaction (i.e., site-specific primer, site-specific Stem primer; mismatch primer, mismatch Stem primer, etc). In still additional embodiments, the first-stage reaction chamber comprises a channel that is in one-way fluid communication with one or more additional containers or chambers comprising primers for performing the second-stage amplification reaction.

In any of the aspects or embodiments described herein, the first-stage amplification reaction is an isothermal nucleic acid amplification reaction. In certain embodiments, the second-stage amplification reaction is an isothermal nucleic acid amplification reaction. In additional embodiments, both the first-stage amplification reaction, and the second-stage amplification reaction are isothermal nucleic acid amplification reactions. In certain embodiments, the first-stage and/or second-stage amplification reaction is a LAMP-based isothermal amplification reaction. In a preferred embodiment, the first-stage amplification is a LAMP-based isothermal amplification reaction and the second-stage is a LAMP-STEM-based isothermal amplification reaction.

In any of the aspects or embodiments described herein, the mismatch primer comprises a 3' end terminal nucleotide mismatch. In certain embodiments, a site-specific primer as described herein comprises on the 3' terminal end a nucleotide complementary to a nucleotide of interest in the target nucleic acid template.

In another aspect the description provides a two-stage method of diagnosing a genetic disease, SNP, viral or microbial infection wherein said method comprises providing a nucleic acid sample from subject to be tested, performing the two-stage amplification reaction as described herein, wherein the site-specific primer is specific for a region or nucleotide(s) of interest associated with at least one of a genetic disease, mutation, SNP, virus, or bacteria, and wherein an increased rate of amplification with the site-specific primer versus a mismatch primer is indicative of a subject having an allele for the genetic disease, mutation, SNP, virus or microbe. In certain embodiments, the microbe is a bacterium.

In certain embodiments, the method of diagnosing a disease or pathogenic infection comprises the step of treating the patient testing positive for the nucleotide of interest with an appropriate therapeutic, e.g., antibiotic, drug, etc.

In any of the aspects or embodiments described herein, the method further comprises a step of detecting the formation of an amplicon. In certain embodiments, the amplification reaction mixture comprises a fluorescently labeled dNTPs or a fluorescent DNA intercalating dye. In certain embodiments, formation of an amplicon is detected in real-time by measuring an increase in fluorescence.

In any of the aspects or embodiments described herein, the nucleic acid template comprises a plurality of primer binding regions, wherein the primers serve as origins of synthesis and define a polynucleotide region (i.e., "an amplicon") to be amplified using a polymerase.

In any of the embodiments described herein, the method further comprises the addition of at least one Displacement or bumper primer in the amplification reaction.

In any of the embodiments described herein, the target nucleic acid template comprises genomic DNA, cDNA or RNA or a segment therefrom, from a virus, plant, microbe, or multicellular organism, e.g., a mammal, such as a human. In certain embodiments, the genomic DNA is from a pathogenic virus or microbe, e.g., bacteria or archae. In certain embodiments, the target nucleic acid template is from *tubercle bacillus* (MTB or TB). In certain additional embodimetns, the target nucleic acid template is from the rpoB gene from MTB. In still further embodiments, the target nucleic acid template is rpoB13.5 F6.

In any of the embodiments described herein, the method further comprises the addition of at least one loop primer which is complementary to a region in the first loop or the second loop of the amplicon.

In any of the embodiments described herein, the first-amplification reaction is preceeded by a heating step in which the target nucleic acid template and primers are heated to approximately 95° C. for from about 1 minute to about 15 mintues. In certain embodiments, the target nucleic acid template and primers are heated to approximately 95° C. for from about 5 minutes to about 10 minutes.

In any of the embodiments described herein, the amplification reaction is performed at a temperature of from about 50° C. to about 75° C. In certain embodiments, the amplification reaction is performed at a temperature of from about 55° C. to about 65° C.

In any of the embodiments described herein, the site-specific primer (e.g., site-specific Stem primer) is in the forward direction. In certain embodiments, the site-specific primer is in the reverse direction. In still additional embodiments, both forward and reverse site-specific primers are included in the reaction.

In any of the embodiments described herein, 3' SNP specific nucleotide is comprised within at least one of a loop-forming primer, a displacement primer, or a loop primer.

In any of the embodiments described herein, the primers or nucleotide reagents comprise a chemical modification.

In any of the embodiments described herein, the first-stage and second-stage amplification reactions are performed sequentially in the same reaction container or chamber. In certain embodiments, the first-stage and second-stage amplification reactions (and any subsequent amplification reactions) are performed sequentially but in different reaction chambers.

In any of the embodiments described herein, the primers can comprise an endonuclease restriction site, or recognition element for a nicking enzyme.

In any of the embodiments described herein, the amplification reaction can comprise a hairpin primer comprising a first and a second segment, wherein the first segment is substantially complementary to a primer binding region on a template and the second segment comprises a sequence that is substantially complementary to another region in the primer.

In any of the embodiments described herein, the amplification reaction can comprise a loop-providing primer, comprising a hairpin primer in which the inverted repeats are separated by a linker region.

In any of the embodiments described herein, the amplification reaction can comprise a chimeric primer.

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

Figure 1:
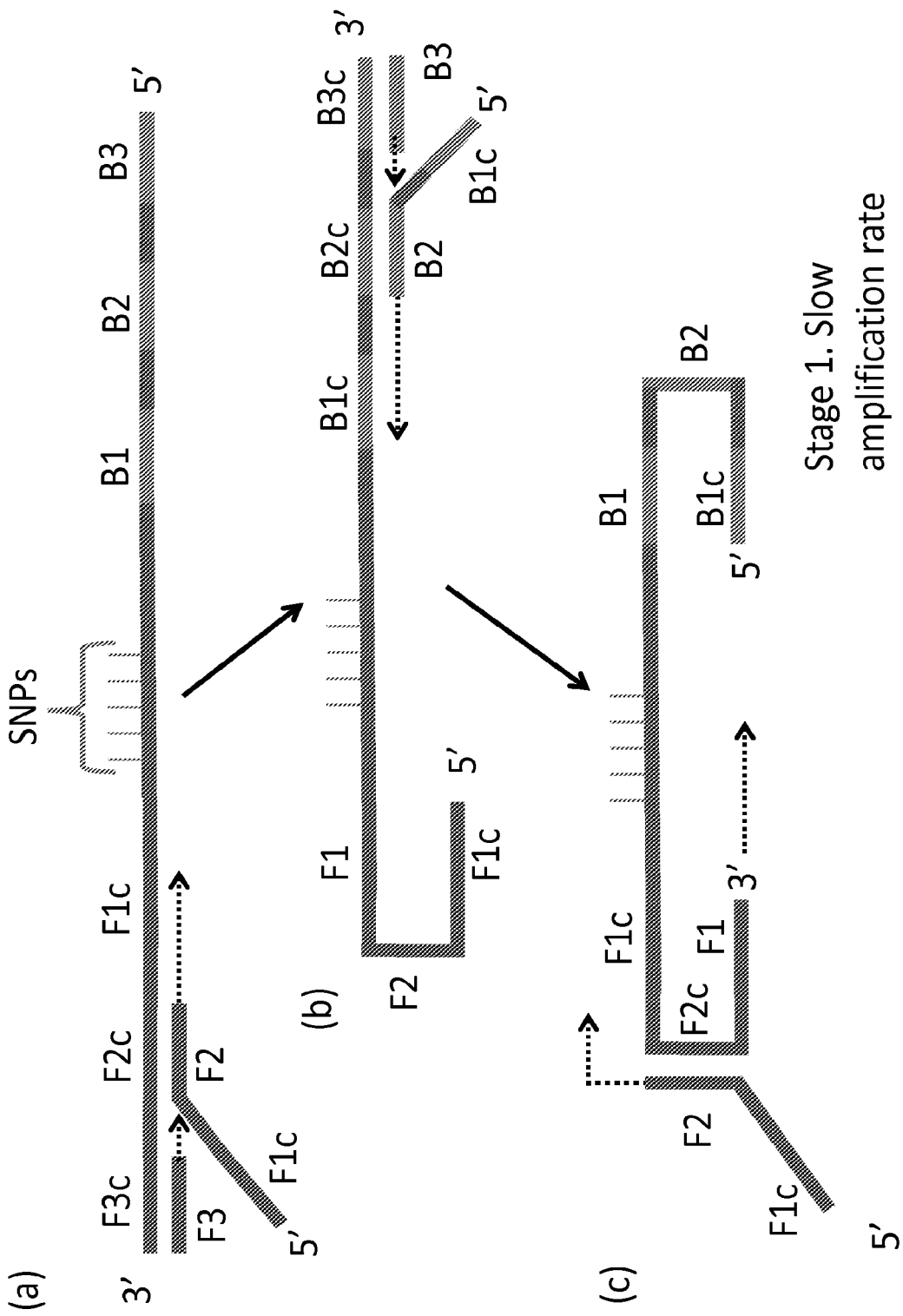
FIG. 1. Illustration of general principle for loop-mediated isothermal amplification (LAMP). In an exemplary method as described herein a first stage isothermal amplification reaction based on the LAMP method is performed, which includes FIP and BIP "loop-forming primers" (LFPs) (comprising F1c and F2, B1c and B2, priming sites, respectively), and "displacement primers" (F3 and B3). The LAMP reaction produces concatamers of the "dumbbell" structure (c). As described herein, the initial LAMP reaction proceeds at a relatively slow rate.

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

The present description provides an improved nucleic acid amplification technique (NAAT), and in particular iNAAT, which is robust, cost-effective, provides for flexibility in primer placement and design, and also demonstrates increased rate, sensitivity, and reproducibility at low copy number, in particular, as compared to, e.g., SDA or LAMP.

As described above, it is advantageous to have a platform that separates amplification samples into multiple separate reactions, so there is no interference of dyes or primers, so that more tests can be reliably performed per sample. In order to do this without diluting the sample and thus reducing sensitivity or inducing non-uniformity between the multiple reaction chambers, the nucleic acids in the sample should be amplified somewhat before being distributed to the final reaction areas. This will ensure that all the downstream reaction chambers have an adequate amount of starting DNA (or RNA) to reliably deliver a meaningful result.

A known way to do this is to use an initial PCR reaction that amplifies a product that contains the regions of interest but is somewhat larger, and then distributes that product to separate downstream reactions that only amplify each small region of interest (or SNP). This is known as nested PCR, since each target sequence or SNP is "nested" within a larger amplified region. If this method is used, a dilution step is typically required so that the pre-amplification primers do not contaminate the final reaction and detection step. A dilution step is highly undesirable in an automated instrument because it requires an additional fluid source and additional manipulations of the sample fluid. It is far simpler and therefore more favorable to be able to use the fluid containing the pre-amplified sample directly in the final amplification and detection reaction.

Another way to do this is to use Irma instead of Thymine in the pre-amplification primers, and then destroy the primers in a subsequent step using an enzyme (that destroys the Uracil), and then using the resulting pre-amp'd but primer-free solution for the final amplification and detection step. This method has the advantage of not requiring the introduction of a dilutent, but requires an additional enzyme, which may be provided dry and immobilized (lyophilized), which may be simpler than a dilution step: it is further desirable to use a method that does not require temperature cycling (isothermal). This is because isothermal amplification reactions tend to be faster than temperature cycling reactions (such as PCR), and because isothermal requirements result in a lower cost and lower power instrument.

Another known method for pre-amplifying a sample is to use whole genome amplification, whereby all of the genetic material in the sample. is amplified equally. This is accomplished using a library of short (6 or 7 base) primers that represent nearly all possible sequences, and can thus cover all genomes. Nearly all nucleic acid samples will be contaminated with nucleic acids from organisms other than the ones of interest, and sometimes there is a factor of over $10^8$ excess of this unwanted genetic material than of the genetic material of interest.

Therefore, for this method, the vast majority of the amplification resources required for this method of pre-amplification will be consumed by the amplification of unwanted, contaminating DNAs. Also, within the nucleic acids of interest, only a tiny portion (0.01% or less typically) of the genome is tested for in the final amplification reaction, so the whole genome amplification method is further miss-directed at non-informative genomic areas by a factor of over $10^{12}$. In addition, whole genome amplification methods take a relatively long time period (hours), and require special, highly processive strand-displacing enzymes, at high concentrations, which add cost to the assay. If too much material is pre-amplified using this method, which could happen in a highly contaminated sample, then a positive signal could result in the final detection area, even if no DNA of interest was present. A dilution step would be required to prevent this false positive signal, which adds cost and complexity to the fluid handling system of an instrument employing this technology.

A method that has neither of the above additional assay requirements and their associated drawbacks is preferred.

The methods as described herein provide for a low-rate isothermal pre-amplification followed by high rate site-specific amplification and detection step. For instance, an exemplary method as described herein includes a first-stage slow rate isothermal reaction followed immediately by a separate or second-stage fast rate exponential isothermal amplification reaction that proceeds at an enhanced rate relative to the first reaction.

In another example, a regionspecific pre-amplification step is done using the LAMP system without the presence of loop primers or stem primers, thus resulting in a very slow exponential reaction speed. Once an amplification of approximately 100-100,000× is achieved (in a predetermined time frame), the reaction is split into multiple reaction chambers, where in each chamber a different set of loop or stem primers are introduced that are site-specific sensitive by virtue of, e.g., a 3' end match/mismatch, or annealing temperature difference, so that the much higher speed exponential reaction only occurs if the loop or stem primers are correctly matched to the sample sequence. The significant difference in amplification rate can be detected by real-time fluorescent measurement of, e.g., an intercalating dye, and thus multiple site-specific reactions within the same region of interest can be individually identified with a single assay.

Thus, in one aspect, the description provides two-stage nucleic acid amplification reaction comprising: providing a target nucleic acid template and at least one primer that anneals to the target nucleic acid template near a region of interest to be amplified; performing a first-stage nucleic acid amplification (or "pre-amp") reaction to amplify the region of interest (amplicon). In certain embodiments, a forward and reverse primer are provided and used to synthesize and amplify the region of interest or amplicon of interest.

Subsequently, the pre-amp reaction product ("primary amplicon" or "amplified region of interest") is utilized in one or more second-stage amplification reactions wherein at leaset one of the reactions includes a site or sequence-specific secondary primer ("site-specific primer"), such that rapid amplification occurs only if a complementary sequence for the site-specific primer (i.e., a site-specific region of interest) exists in the primary amplicon or amplified region of interest from stage-one. In other words, the nucleic acid region of interest from stage-one is positive for the site of interest. As described herein, the appearance of amplification products in each second-stage reaction can be detected and compared simultaneously and in real-time, wherein a fast rate of amplification relative to the first-stage reaction, a second-stage reaction in which no secondary primer is added, and a second-stage mismatch primer reaction is indicative of the presence of the site-specific region of interest.

Significantly, because in certain embodimetns, the region being amplified is the same in both the first-stage and second-stage reactions, it is advantageous to introduce the second-stage amplification reaction primers well before there is a measurable product from the first-stage amplification reaction, otherwise the second-stage amplification product cannot be detected.

The methods as described herein provide for a first-stage, slow-rate isothermal pre-amplification followed by multiple, discrete second-stage amplification and detection reactions performed in parallel directly on the products from the first-stage amplification. At least one of the second-stage reactions includes a site-specific secondary primer, wherein if the primary amplicon template comprises a complementary site for the site-specific primer, the site-specific primer amplification reaction proceeds at a faster rate relative to both the first-stage reaction and second-stage reaction in which no secondary primer is added. In certain embodiments, at least one of the second-stage reactions includes a secondary primer having a mismatch nucleotide ("mismatch primer"), e.g., a 3' mismatch ("3' mismatch primer"), wherein the site-specific primer amplification reaction proceeds at a faster rate relative to the first-stage reaction, second-stage reactions in which no secondary primer is added, and the second-stage mismatch primer reaction.

For example, the description provides a method wherein a first-stage region-specific pre-amplification step is performed, and then the reaction is split into multiple reaction chambers, where in at least one chamber a secondary primer, e.g., loop or stem primer, is introduced that is site-specific sensitive by virtue of, e.g., a 3' end match/mismatch, or annealing temperature difference, so that a much higher speed exponential reaction only occurs if the secondary primer is correctly matched to the sample sequence. The significant difference in amplification rate can be detected by real-time fluorescent measurement of, e.g., an intercalating dye, and thus multiple site-specific reactions within the same region of interest can be individually identified with a single assay.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The term "compound", as used herein, unless otherwise indicated, refers to any specific chemical compound disclosed herein and includes tautomers, regioisomers, geometric isomers, and where applicable, stereoisomers, including optical isomers (enantiomers) and other steroisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

The term "patient" or "subject" is used throughout the specification to describe an animal, preferably a human or a domesticated animal, to whom treatment, including prophylactic treatment, with the compositions according to the present invention is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present invention, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

The terms "nucleic acid," "polynucleotides," and "oligonucleotides" refers to biopolymers of nucleotides and, unless the context indicates otherwise, includes modified and unmodified nucleotides, and both DNA and RNA. For example, in certain embodiments, the nucleic acid is a peptide nucleic acid (PNA). Typically, the methods as described herein are performed using DNA as the nucleic acid template for amplification. However, nucleic acid whose nucleotide is replaced by an artificial derivative or modified nucleic acid from natural DNA or RNA is also included in the nucleic acid of the present invention insofar as it functions as a template for synthesis of complementary chain. The nucleic acid of the present invention is generally contained in a biological sample. The biological sample includes animal, plant or microbial tissues, cells, cultures and excretions, or extracts therefrom. In certain aspects, the biological sample includes intracellular parasitic genomic DNA or RNA such as virus or mycoplasma. The nucleic acid may be derived from nucleic acid contained in said biological sample. For example, genomic DNA, or cDNA synthesized from mRNA, or nucleic acid amplified on the basis of nucleic acid derived from the biological sample, are preferably used in the described methods.

The term "primer" or "oligonucleotide primer" can refer to a short polynucleotide that satisfies the requirements that it must be able to form complementary base pairing sufficient to anneal to a desired nucleic acid template, and give an —OH group serving as the origin of synthesis of complementary chain at the 3'-terminal. Accordingly, its backbone is not necessarily limited to the one via phosphodiester linkages. For example, it may be composed of a phosphothioate derivative having S in place of O as a backbone or a peptide nucleic acid based on peptide linkages. The bases may be those capable of complementary base pairing. In the nature, there are 5 bases, that is, A, C, T, G and U, but the base can be an analogue such as bromodeoxyuridine. The oligonucleotides as used herein can function not only as the origin of synthesis but also as a template for synthesis of complementary chain. The term polynucleotide includes oligonucleotides, which have a relatively short chain length. Signficantly, a primer need not be fully complementary in order to anneal to a binding site on a polynucleic acid.

In certain embodiments, the primer is complementary to the binding site sequence. In other embodiments, the primer comprises one or more mismatched nucleotides (i.e., bases that are not complementary to the binding site). In still other embodiments, the primer can comprise a segment that does not anneal to the polynucleic acid or that is complementary to the inverse strand of the polynucleic acid to which the primer anneals. In certain embodiments, a primer is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length. In a preferred embodiment, the primer comprises from 2 to 100 nucleotides.

Oligonucleotides can be used to hybridize with genomic DNA or cDNA sequences in the same or different organisms. Those of skill in the art will appreciate that various degrees of stringency of hybridization can be employed in the assay. The degree of complementarity (sequence identity) required for detectable binding will vary in accordance with the stringency of the hybridization medium and/or wash medium. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. Minor sequence variations in the probes and primers can be compensated for by reducing the stringency of the hybridization.

"Complementarity" refers to the ability of a nucleic acid to form hydrogen bond(s) or hybridize with another nucleic acid sequence by either traditional Watson-Crick or other non-traditional types. As used herein "hybridization," refers to the binding, duplexing, or hybridizing of a molecule only to a particular nucleotide sequence under low, medium, or highly stringent conditions, including when that sequence is present in a complex mixture (e.g., total cellular) DNA or RNA. See e.g. Ausubel, et al., CURRENT PROTOCOLS IN MOLECULAR BIOLOGY, John Wiley & Sons, New York, N.Y., 1993.

If a nucleotide at a certain position of a polynucleotide is capable of forming a Watson-Crick pairing with a nucleotide at the same position in an anti-parallel DNA or RNA strand, then the polynucleotide and the DNA or RNA molecule are complementary to each other at that position. The polynucleotide and the DNA or RNA molecule are "substantially complementary" to each other when a sufficient number of corresponding positions in each molecule are occupied by nucleotides that can hybridize or anneal with each other in order to effect the desired process. A complementary sequence is a sequence capable of annealing under stringent conditions to provide a 3'-terminal serving as the origin of synthesis of complementary chain.

"Forward primer binding site" and "reverse primer binding site" refers to the regions on the template DNA and/or the amplicon to which the forward and reverse primers bind. The primers act to delimit the region of the original template polynucleotide which is exponentially amplified during amplification. In some embodiments, additional primers may bind to the region 5' of the forward primer and/or reverse primers. Where such additional primers are used, the forward primer binding site and/or the reverse primer binding site may encompass the binding regions of these additional primers as well as the binding regions of the primers themselves. For example, in some embodiments, the method may use one or more additional primers which bind to a region that lies 5' of the forward and/or reverse primer binding region. Such a method was disclosed, for example, in WO0028082 which discloses the use of "displacement primers" or "outer primers".

The term "template" used in the present invention means nucleic acid serving as a template for synthesizing a complementary chain in a nucleic acid amplification technique. A complementary chain having a nucleotide sequence complementary to the template has a meaning as a chain corresponding to the template, but the relationship between the two is merely relative. That is, according to the methods described herein a chain synthesized as the complementary chain can function again as a template. That is, the complementary chain can become a template. In certain embodiments, the template is derived from a biological sample, e.g., plant, animal, virus, micro-organism, bacteria, fungus, etc. In certain embodiments, the animal is a mammal, e.g., a human patient.

"Patient sample" refers to any sample taken from a patient and can include blood, stool, swabs, sputum, Broncho Alveolar Lavage Fluid, tissue samples, urine or spinal fluids. Other suitable patient samples and methods of extracting them are well known to those of skill in the art. A "patient" or "subject" from whom the sample is taken may be a human or a non-human animal. When a sample is not specifically referred to as a patient sample, the term also comprises samples taken from other sources. Examples include swabs from surfaces, water samples (for example waste water, marine water, lake water, drinking water), food samples, cosmetic products, pharmaceutical products, fermentation products, cell and micro-organism cultures and other samples in which the detection of a micro-organism is desirable.

In the present invention, the terms "synthesis" and "amplification" of nucleic acid are used. The synthesis of nucleic acid in the present invention means the elongation or extension of nucleic acid from an oligonucleotide serving as the origin of synthesis. If not only this synthesis but also the formation of other nucleic acid and the elongation or extension reaction of this formed nucleic acid occur continuously, a series of these reactions is comprehensively called amplification.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, Md.).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215:403-410 (1990)). The BLAST X program is publicly available from NCBI and other sources (BLAST Manual, Altschul, S., et al., NCBINLM NIH Bethesda, Md. 20894: Altschul, S., et al., J. Mol. Biol. 215:403-410 (1990). The well-known Smith Waterman algorithm may also be used to determine identity.

A "single-nucleotide polymorphism" (SNP) is a DNA sequence variation occurring commonly within a population (e.g. 1%) in which a single nucleotide—A, T, C or G—in the genome (or other shared sequence) differs between members of a biological species or paired chromosomes. For example, two sequenced DNA fragments from different individuals, AAGCCTA to AAGCTTA, contain a difference in a single nucleotide (i.e., there are two alleles). Almost all common SNPs have only two alleles. SNPs can occur in coding, non-coding or intergenic regions of DNA. The genomic distribution of SNPs is not homogenous; SNPs occur in non-coding regions more frequently than in coding regions or, in general, where natural selection is acting and 'fixing' the allele (eliminating other variants) of the SNP that constitutes the most favorable genetic adaptation. Other factors, like genetic recombination and mutation rate, can also determine SNP densi. SNPs within a coding sequence do not necessarily change the amino acid sequence of the protein that is produced, due to degeneracy of the genetic code.

SNPs in the coding region are of two types, synonymous and nonsynonymous SNPs. Synonymous SNPs do not affect the protein sequence while nonsynonymous SNPs change the amino acid sequence of protein. The nonsynonymous SNPs are of two types: missense and nonsense. SNPs that are not in protein-coding regions may still affect gene splicing, transcription factor binding, messenger RNA degradation, or the sequence of non-coding RNA. Gene expression affected by this type of SNP is referred to as an eSNP (expression SNP) and may be upstream or downstream from the gene.

As there are for genes, bioinformatics databases exist for SNPs. dbSNP is a SNP database from the National Center for Biotechnology Information (NCBI). Kaviar is a compendium of SNPs from multiple data sources including dbSNP. SNPedia is a wiki-style database supporting personal genome annotation, interpretation and analysis. The OMIM database describes the association between polymorphisms and diseases (e.g., gives diseases in text form), the Human Gene Mutation Database provides gene mutations causing or associated with human inherited diseases and functional SNPs, and GWAS Central allows users to visually interrogate the actual summary-level association data in one or more genome-wide association studies. The International SNP Map working group mapped the sequence flanking each SNP by alignment to the genomic sequence of large-insert clones in Genebank. Another database is the International HapMap Project, where researchers are identifying Tag SNP to be able to determine the collection of haplotypes present in each subject.

The polynucleic acid produced by the amplification technology employed is generically referred to as an "amplicon" or "amplification product." The nature of amplicon produced varies significantly depending on the NAAT being practised. For example, NAATs such as PCR may produce amplicon which is substantially of identical size and sequence. Other NAATs produce amplicon of very varied size wherein the amplicon is composed of different numbers of repeated sequences such that the amplicon is a collection of concatamers of different length. The repeating sequence from such concatamers will reflect the sequence of the polynucleic acid which is the subject of the assay being performed.

In the present specification, the simple expression "5'-side" or "3'-side" refers to that of a nucleic acid chain serving as a template, wherein the 5' end generally includes a phosphate group and a 3' end generally includes a free —OH group.

The term "disease state or condition" is used to describe any disease state or condition, in particular, those relating to genetic abnormalities or due to the presence of a pathogenic organism such as a virus, bacteria, archae, protozoa or multicellular organism.

Methods

As described herein, it has been surprisingly and unexpectedly discovered that performing a two-stage nucleic acid amplification reaction using primers that provide for differential reaction rates depending on the presence or absence of specific sequences of interest allows for the rapid, real-time detection of nucleic acid sequences of interest, which provides advantages for point-of-care diagnosis.

In one aspect, the description provides two-stage nucleic acid amplification reaction comprising: providing a target nucleic acid template and at least one primer that anneals to the target nucleic acid template near a region of interest to be amplified; performing a first-stage nucleic acid amplification (or "pre-amp") reaction to amplify the region of interest (amplicon). In certain embodiments, a forward and reverse primer are provided and used to synthesize and amplify the region of interest or amplicon of interest.

Subsequently, the first-stage pre-amp reaction product ("primary amplicon" or "amplified region of interest") is utilized in one or more discrete second-stage nucleic acid amplification reactions, wherein in at least one second-stage reactiona site-specific primer is included, such that rapid or accelerated amplification occurs only if a complementary sequence for the site-specific primer (i.e., site-specific region of interest) exists in the primary amplicon. Stated differently, if the rate of second-stage amplification reaction is accelerated relative to the stage-one reaction, and any second-stage reactions lacking an additional primer, and/or second-stage reactions having a mismatch primer, the nucleic acid region of interest from stage-one is positive for the site of interest.

Thus, according to certain methods described herein, the rate of the second-stage reaction is selectively enhanced relative to the first by the presence of specific primer binding sequences that are fully complementary or at least complementary to the 3' end of the second-stage primer (herein, the "site-specific primer"). In a certain embodiments, the relative amplification reaction rates are as follows: second-stage site-specific primer amplification>>first-stage amplification reaction. In still additional embodiments, the relative amplification reaction rates are as follows: second-stage site-specific primer amplification>>first-stage reaction≈second-stage mismatch primer amplification. As used herein, the term "mismatch primer" generally refers to a primer having a 3' end nucleotide that is not complementary to the primer binding site on the template.

Figure 5:
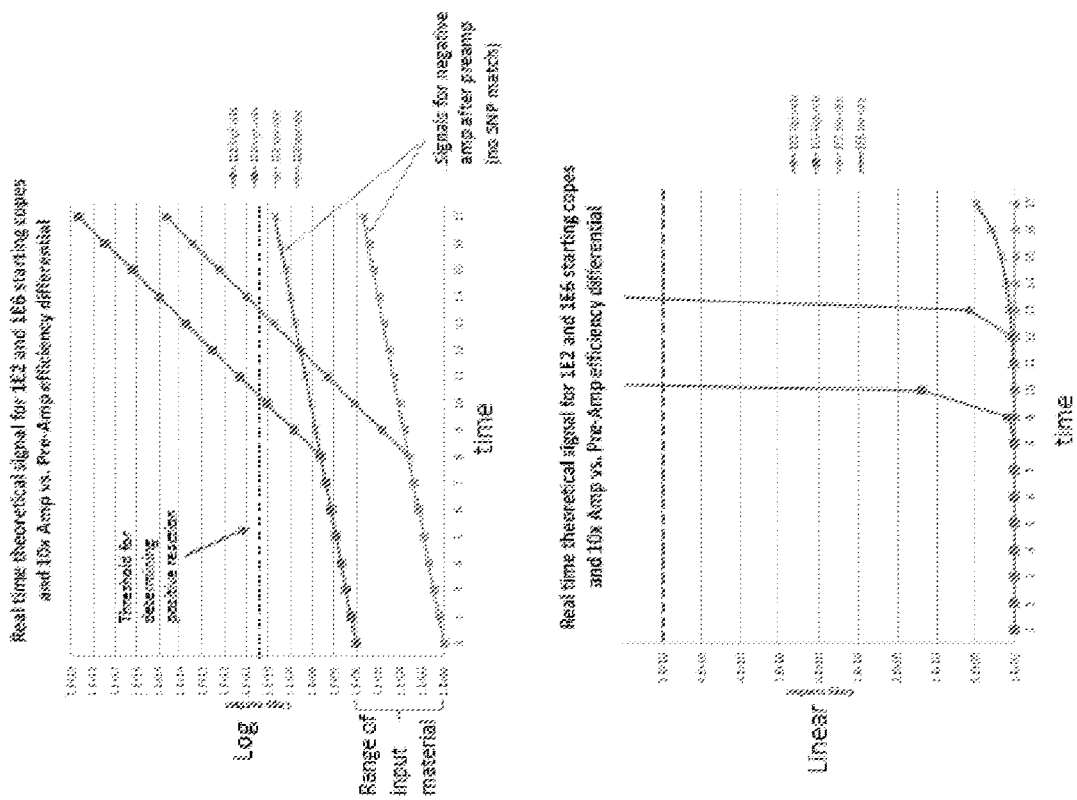
FIG. 5. Real-time theoretical signal for $10^2$ and $10^6$ starting copies and 10× second-stage amplification efficiency versus first-stage reaction efficiency. The upper panel shows the two exponential reactions rates on a log scale, and the lower panel shows them on a linear scale. The vertical axis represents the number of copies of amplicon present; both input material and amplified material. This axis also represents the signal that can be generated and detected using an intercalating dye. The dashed horizontal line represents the limit of detection of an instrument that is measuring the fluorescence signal that can be generated by said dye. The horizontal axisof both graphs represent time in miniutes. The 8-minute time point is the point at which the second-stage primers are added to the reaction. This is where the accelerated reaction starts if the second-stage primer(s) are matched to a site within the primary amplicon that was generated by the first reaction, which is represented by the lines with increased slopes in the log chart. The continuation of the lower slope lines on the log chart indicates the signal that would be present if the secondary primers do not match the site of interest within the amplicon.

As indicated above, the differential relative amplification reaction rates between the first-stage, and second-stage, as well as between the second-stage site-specific primer versus second-stage mismatch primer are important for being able to selectively detect for the presence (i.e., amplification) of the site of interest. For example, FIG. 5 demonstrates that the first-stage pre-amplification reaction proceeds relatively slowly to the threshold signal level (i.e., the Cq is longer). However, in the presence of a complementary primer, the second-stage amplification reaction proceeds exponentially (i.e., the Cq for the complementary primer is faster than that of both the first-stage reaction, and second-stage mismatch primer reaction).

In certain embodiments, the second-stage amplification rate is exponential. In certain embodiments of the methods described herein, the second-stage site-specific primer reaction rate is at least about 5, 10, 20, 25, 30, 35, 40, 45, 50, 55, 60, 65, 70, 75, 80, 85, 90, 95, 100, 500, 1000, 10000, 100000 or more times faster than the second-stage mismatch primer reaction. In certain embodiments of the methods described herein, the second-stage site-specific primer reaction rate is about 5, 10, 20, 25, 30, 35, 40, 45, 50, 55, 60, 65, 70, 75, 80, 85, 90, 95, 100, 500, 1000, 10000, 100000 or more times faster than the second-stage mismatch primer reaction.

In certain embodiments of the methods described herein, the resulting Cq (time to positive detection of the reaction) for the second-stage site-specific primer reaction is at least about 10%, 15%, 20%, 25%, 30%, 35%, 40%, 45%, 50%, 55%, 60%, 65%, 70%, 75%, 80%, 85%, 90%, 95%, 100%, 500%, 1000%, 10000% or more faster than the second-stage mismatch primer reaction. In certain embodiments of the methods described herein, the resulting Cq (time to positive detection of the reaction) for the second-stage site-specific primer reaction is about 10%, 15%, 20%, 25%, 30%, 35%, 40%, 45%, 50%, 55%, 60%, 65%, 70%, 75%, 80%, 85%, 90%, 95%, 100%, 500%, 1000%, 10000% or more faster than the second-stage mismatch primer reaction. In certain embodiments of the methods described herein, the resulting Cq (time to positive detection of the reaction) for the second-stage site-specific primer reaction is at least about 25% faster than the second-stage mismatch primer reaction. In certain embodiments of the methods described herein, the resulting Cq (time to positive detection of the reaction) for the second-stage site-specific primer reaction is from about 10% to about 1000%, from about 20% to about 500%, or from about 25% to about 100% faster than the second-stage mismatch primer reaction. However, the important factor is that the differential in time be far enough above the variability of the system to confidently distinguish which second-stage reaction is matched (i.e., the second-stage primer is complementary to the primer binding site on the template, in particular at the 3' end).

As described below, in certain embodiments the first-stage amplification reaction is a relatively slow LAMP-based amplification. In additional embodiments, the second-stage amplification reaction is a relatively rapid LAMP-STEM-based amplification, wherein the reaction rate is enhanced by the binding of site-specific Stem primers to the site of interest. As such, the methods as described herein provide for robust, rapid, efficient, and highly specific amplification of desired genetic sequences. The amplification of the desired amplicons can be monitored or detected by any known method, including, e.g., intercalating dyes, labeled reagents, etc.

In certain embodiments, the site-specific primer is a site-specific Stem primer. In certain embodiments, the mismatch primer is a mismatch Stem primer. In any of the embodiments described herein, the mismatch primer comprises at least one mismatched nucleotide (i.e., a nucleotide that is not complementary to the template). In certain embodiments, the mismatched nucleotide is at the 3' end of the mismatch primer ("3' mismatch primer").

In certain embodiments, the site-specific primer and the mismatch primer comprise at their 3' ends, respectively, a nucleotide that is specific or complementary to one form of a multi-allelic or polymorphic site such that, depending on which allele or polymorphism the nucleic acid template comprises, the site-specific primer could comprise a 3' end nucleotide mismatch, and the mismatch primer could contain the 3' end complementary nucleotide. In other words, in certain embodiments, the method comprises performing a plurality of second-stage amplification reactions, wherein each reaction comprises a primer that is specific for a particular allele. However, as described herein, only those amplification reactions comprising a secondary primer that is complementary at its 3' end to the site of interest will proceed at an increased rate relative to the first-stage reaction, and relative to the second-stage reaction comprising a 3' mismatch.

In certain embodiments, the method comprises performing a plurality of second-stage amplification reactions, wherein each respective reaction comprises a site-specific or allele-specific primer. In certain embodiments, each site-specific primer in each of the respective second-stage amplification reactions is specific for a different allele, mutation or polymporphism. In such a configuration, the methods provide for a multiplexing method for determining the presence or absence of multiple polymorphisms simultaneously. The methods as described are, therefore, particularly advantageous for differentiating between multi-allelic genes, genotypes, clades, forms, groups, subgroups, classes, species or strains. For example, certain pathogenic bacteria are closely related to non-pathogenic strains or species. As such, in an exemplary aspect, the current description provides methods comprisign multiple second-stage reactions, wherein each respective reaction comprises a primer (or primer pair) that is specific for a site or allele of interest that allows for the simultaneous determination of, e.g., species and strain of a microbe.

For example, in one embodiment, the description provides a two-stage nucleic acid amplification and real-time detection method comprising
  a. providing a target nucleic acid template and at least one primer that anneals to the target nucleic acid template near a region of interest to be amplified;
  b. performing a first-stage nucleic acid amplification reaction to amplify the region of interest, thereby forming aprimary amplicon;
  c. dividing (b) into at least tworeactions, including in at least one of the reactions a secondary site-specific primer that is complementary to a site-specific primer binding region (i.e., a site-specific region of interest) in the primary amplicon and defines a site of interest, and including at least onereaction in which no secondary primer is included;
  d. performing a second nucleic acid amplification reaction thereby amplifying the region of interest; and
  e. detecting and comparing in real-time the amplification rate of the site-specific primer reaction and the mismatch primer reaction, wherein an enhanced rate of amplification in the site-specific primer reaction relative to the mismatch primer reaction is indicative of the presence of the site of interest. In certain embodiments, a forward and reverse primer are provided and used to synthesize and amplify the region of interest or amplicon of interest.

In any of the aspects or embodiments described herein, the mismatch primer comprises a 3' end terminal nucleotide mismatch. In any of the aspects or embodiments described herein, a site-specific primer can comprise on the 3' terminal end a nucleotide that is complementary to a nucleotide of interest in the target nucleic acid template. In certain embodiments, the site-specific primer comprises a nucleotide mismatch at a site other than the 3' terminus.

In certain embodiments, multiple second-stage nucleic acid amplification reactions are performed in parallel. In a preferred embodiment, the site-specific primer reaction is performed and monitored in parallel with a separate reaction in which similar site-specific primers are used but that comprise a mismatch in its nucleic acid sequence. In other words, in one reaction the site-specific primer is fully complementary to a site of interest on the target nucleic acid, and in another reaction, the primer anneals to the same site but comprises a mismatch, e.g., a 3' end mismatch. The inventors have discovered that a mismatch in the site-specific primer slows the amplification reaction rate enough such that by direct, real-time detection or montoring and comparing of both amplifications reactions in parallel it is possible to identify the presence or absence of sequence variances that exist in the nucleic acid sample. Stated differently, the rate of the second amplification reaction is selectively enhanced or suppressed based on the presence of a sequence that is complementary to the site-specific primer. Without being bound by any particular theory, it is believed that the rate of the second-stage amplification is enhanced by the use of the site-specific primer because it serves as another origin of extension.

In another aspect, a method is described comprising performing multiple, separate or discrete second-stage amplification reactions utilizing the first-stage amplification product in which the rate of the second-stage amplification reaction is compared as between at least one reaction having a site-specific primer complementary to a region or sequence of interest on the template, and a reaction having a primer that anneals to the same site but comprises a base-pair mismatch (herein, "a mismatch primer"), wherein a faster reaction rate relative to the other is indicative of the presence or absence of the specific site or region of interest.

In certain embodiments, the method includes performing at least one additional second-stage amplification reaction in parallel with the site-specific and mismatch amplification reactions, wherein no additional primers are added, and monitoring and comparing in real-time the rate of the second-stage amplification reaction comprising the site-specific primer, the reaction comprising the mismatch primer, and the reaction comprising no primer, wherein an enhanced reaction rate relative to the others is indicative of the presence of the specific site or region of interest.

The target template used in the present invention may be any polynucleic acid that comprises suitable primer binding regions that allow for amplification of a polynucleic acid of interest. The skilled person will understand that the forward and reverse primer binding sites need to be positioned in such a manner on the target template that the forward primer binding region and the reverse primer binding region are positioned 5' of the sequence which is to be amplified on the sense and antisense strand, respectively.

The target template may be single or double stranded. Where the target template is a single stranded polynucleic acid, the skilled person will understand that the target template will initially comprise only one primer binding region. However, the binding of the first primer will result in synthesis of a complementary strand which will then contain the second primer binding region.

The target template may be derived from an RNA molecule, in which case the RNA needs to be transcribed into DNA before practising the method of the invention. Suitable reagents for transcribing the RNA are well known in the art and include, but are not limited to, reverse transcriptase.

The methods as described herein can be practiced with any NAAT. For example, known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et at; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.).

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

In certain aspects, the NAAT that is utilized in the methods described herein are isothermal nucleic acid amplification techniques. Some isothermal amplification techniques are dependent on transcription as part of the amplification process, for example Nucleic Acid Sequence Based Amplification (NASBA; U.S. Pat. No. 5,409,818) and Transcription Mediated Amplification (TMA; U.S. Pat. No. 5,399,491) while others are dependent on the action of a Helicase or Recombinase for example Helicase Dependent Amplification (HDA; WO2004027025) and Recombinase polymerase amplification (RPA; WO03072805) respectively, others still are dependent on the strand displacement activity of certain DNA polymerases, for example Strand Displacement Amplification (SDA; U.S. Pat. No. 5,455, 166), Loop-mediated Isothermal Amplification (LAMP; WO0028082, WO0134790, WO0224902), Chimera Displacement Reaction (RDC; WO9794126), Rolling Circle Amplification (RCA; Lizardi, P. M. et al. Nature Genetics, (1998) 19.225-231), Isothermal Chimeric Amplification of Nucleic Acids (ICAN; WO0216639), SMart Amplification Process (SMAP; WO2005063977), Linear Isothermal Multimerization Amplification (LIMA; Isothermal amplification and multimerization of DNA by Bst DNA polymerase, Hafner G. J., Yang I. C., Wolter L. C., Stafford M. R., Giffard P. M, BioTechniques, 2001, vol. 30, no 4, pp. 852-867) also methods as described in U.S. Pat. No. 6,743,605 (herein referred to as 'Template Re-priming Amplification' or TRA) and WO9601327 (herein referred to as 'Self Extending Amplification' or SEA).

A characteristic of these NAATs is that they provide for both copying of a polynucleic acid via the action of a primer or set of primers and for re-copying of said copy by a reverse primer or set of primers. This enables the generation of copies of the original polynucleic acid at an exponential rate.

With reference to NAATs in general it is helpful to differentiate between the physical piece of nucleic acid being detected by the method, from the first copy made of this original nucleic acid, from the first copy of the copy made from this original nucleic acid, from further copies of this copy of a copy. For the sake of clarity, the nucleic acid whose provenance is from the sample being analysed itself will be referred to as the "target nucleic acid template." With referenct to the two-stage method described herein, the first-stage primer-dependent amplification reaction is relatively slow as compared to the second-stage reaction.

As would be understood by the skilled artisan, the primer-generated amplicon gives rise to further generations of amplicons through repeated amplification reactions of the target nucleic acid template as well as priming of the amplicons themselves. It is possible for amplicons to be comprised of combinations with the target template.

The amplicon may be of very variable length as the target template can be copied from the first priming site beyond the region of nucleic acid delineated by the primers employed in a particular NAAT. In general, a key feature of the NAAT will be to provide a method by which the amplicon can be made available to another primer employed by the methodology so as to generate (over repeated amplification reactions) amplicons that will be of a discrete length delineated by the primers used. Again, a key feature of the NAAT is to provide a method by which the amplicons are available for further priming by a reverse primer in order to generate further copies. For some NAATs, the later generation amplicons may be substantially different from the first generation amplicon, in particular, the formed amplicon may be a concatamer of the first generation amplicon.

Methods which produce amplicons in the form of concatamers directly from linear target templates include LAMP (including, LAMP-STEM), TRA, SEA and SMAP (the latter is a hybrid of LAMP and SEA). In each case the concatamers arise from processes involving the first generation amplicon. Thus, it is preferred that synthesis of the polynucleic acid is performed using a NAAT selected from the group consisting of LAMP, TRA, SEA and SMAP. In each case therefore, the invention is associated with a NAAT which provides one or more primers with the capability of producing a concatamer directly from a linear target template.

The methods as described are preferably perfomed with a NAAT that results in the formation of template concatamers. The term "concatamer" as used herein refers to a polynucleic acid having substantially similar nucleotide sequences linked alternately in a single-stranded chain. These arrayed sequences may be simple repeats of each other, inverted repeats or combinations thereof. Further, the process is understood to be repeated by the next generation amplicons such that longer and longer concatamers can be formed.

NAATs which are suitable for the generation of concatamers are well known in the art and generally include "isothermal" amplification techniques. This means that the amplification of the polynucleic acid does not require a change in the incubation temperature, contrary to known thermocycling techniques, such as polymerase chain reaction. For example, isothermal amplification methods include, e.g., SDA, LAMP, LAMP-STEM as described above, can be used in conjunction with the methods described herein.

A common feature of LAMP, TRA, SMAP and SEA is therefore that of first generation amplicon dependent priming, i.e. where the first generation amplicon acts as a primer itself, whether by an intra-molecular event or inter-molecular event, leading to next generation amplicon that is larger in size than the first generation amplicon and which is concatameric in nature. In fact, it is a characteristic of these NAATs that longer and longer amplicon is generated from shorter amplicon such that the number of binding sites for stem primers increases exponentially during the amplification process and hence the ability for stem primers to accelerate amplification. Appreciation of the mechanism of action of the primers generating the concatamers in these NAATs is helpful in understanding how stem primers have their effect. Furthermore, the skilled person aware of the mechanisms which lead to generation of a concatamer will readily be able to identify other suitable NAATs which can be used in the methods of the present invention.

In certain embodiments described herein, the first-stage amplification reaction is an isothermal nucleic acid amplification reaction. In certain embodiments, the second-stage amplification reaction is an isothermal nucleic acid amplification reaction. In additional embodiments, both the first-stage amplification reaction, and the second-stage amplification reaction are isothermal nucleic acid amplification reactions. In certain embodiments, the first-stage and/or second-stage amplification reaction is a LAMP-based isothermal amplification reaction. In a preferred embodiment, the first-stage amplification is a LAMP-based isothermal amplification reaction and the second-stage is a LAMP-STEM-based isothermal amplification reaction, wherein the site-specific primer accelerates the amplification rate (relative to the first amplification reaction), and allows for earlier detection of amplification products relative to the 3' mismatched primer.

In certain embodiments, In addition to the forward and reverse primer binding regions, the target template needs to comprise a stem region that needs to have a sufficient length to allow binding of the one or more stem primers (e.g., site-specific Stem primer or mismatch Stem primer), as described herein. Thus it is preferred that the stem region has a length of at least 5 nucleotides, at least 10 nucleotides, at least 15 nucleotides, at least 20 nucleotides, at least 30 nucleotides, at least 50 nucleotides, at least 100 nucleotides at least 200 nucleotides, at least 300 nucleotides or at least 500 nucleotides.

WO0028082 describes the use of loop-forming primers (LFPs), where a LFP is understood to comprise a first and second segment, wherein the first segment is substantially complementary to a primer binding region on the template and the second segment comprises a sequence that is substantially complementary to a region in the amplicon generated from the first segment of the first primer such that the second segment is able to form a loop, and mentions that the NAAT uses two "outer primers" in addition to the LFPs. These primers are characterised in that the "first outer primer" binds 3' to the "F2" site in the template (i.e. the first outer primer binds the "F3" site, FIG. 1) and the "second outer primer" binds 3' to the binding region of the second LFP, the "R2c" site (i.e. the second outer primer binds the "R3c" site, FIG. 1). Thus, these primers do not bind in the stem-region of the amplicon, which lies 5' of the primer binding sites of the LFPs.

A primer employed in LAMP generates single stranded loops in the amplicon and is referred to herein as "loop forming primer." Loop-forming primer, as used herein, refers to primers which comprise a first and a second segment, wherein the first segment is substantially complementary to the primer binding region on the template and the second segment comprises a sequence that is substantially complementary to a region in the amplicon generated from the first segment of the first primer such that the second segment is able to form a loop. The general structure of loop-forming primers is shown in FIG. 1. The first (and next) generation amplicon resulting from the priming of the target template by a loop-forming primr contains a loop of single stranded polynucleotide flanked by double-stranded polynucleotide formed from Watson-Crick base-pairing of the inverted repeat sequence. The single-stranded loop of polynucleotide is understood to be available for binding by a further primer employed by the NAAT in question but specifically not by a stem primer.

The primer oligonucleotides the present description can be prepared by any method known in the art, including by direct chemical synthesis (see, e.g., Ausubel, et al., supra). Chemical synthesis generally produces a single-stranded oligonucleotide, which can be converted into double-stranded DNA by hybridization with a complementary sequence or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Nucleic acid extension is facilitated by a DNA polymerase, for example, a thermostable strand-displacing (SD) DNA polymerase. Because of the thermostable SD polymerase, there is no need for thermocycling. Displacement or bumper primers (F3 and B3) can be included to facilitate displacement of the FIP and BIP primers, and allow more efficient extension of the complementary DNA strand.

Figure 2:
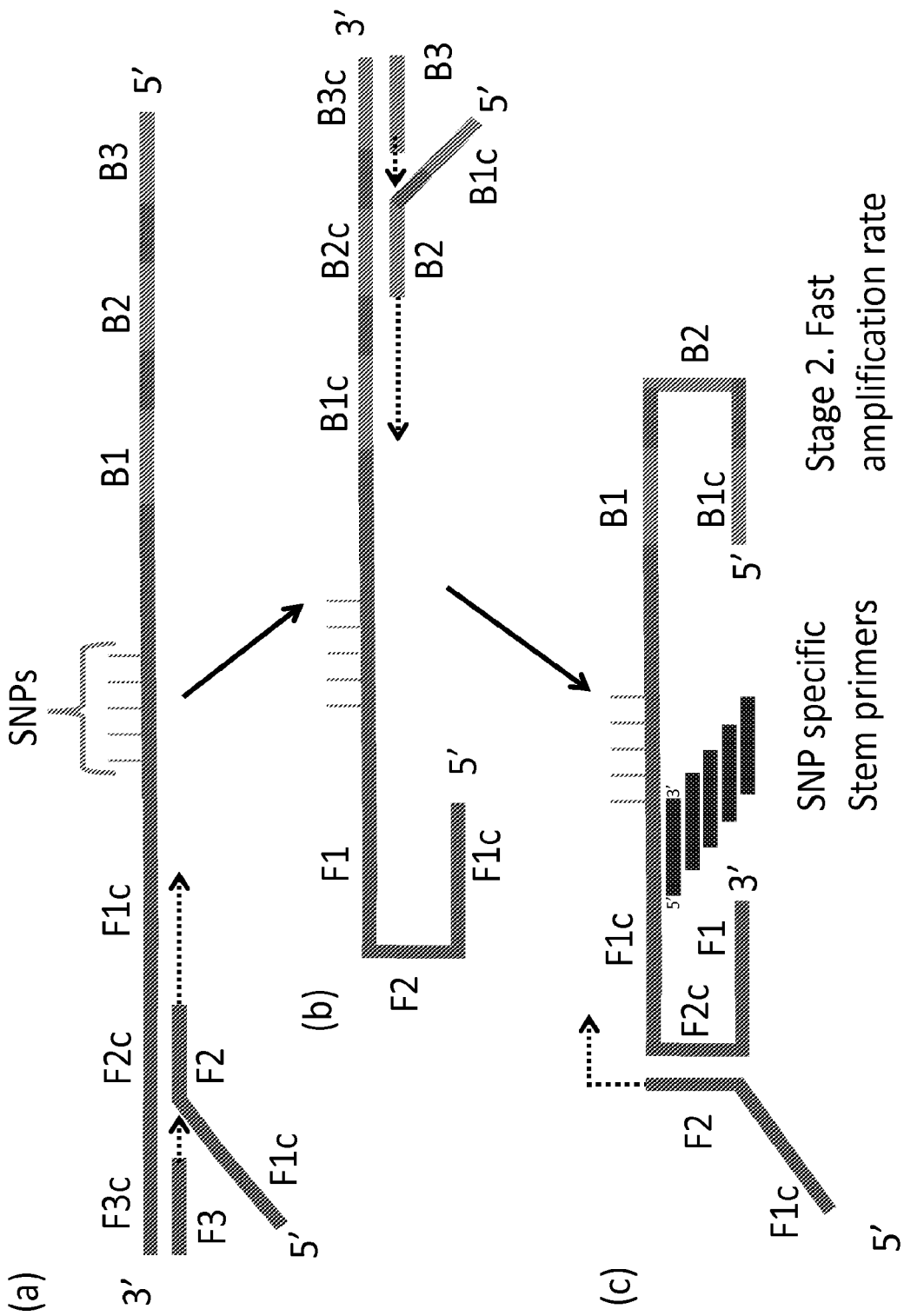
FIG. 2. Illustration of general principal for an exemplary modified LAMP-STEM technique as described herein. As described herein, a LAMP-STEM amplication reaction is performed as the second-stage. The reaction includes at least one "site-specific Stem primer," which is complementary to a location or sequence of interest in the amplicon from the stage-one amplification reaction. The site-speific Stem primer reaction is performed in parallel with separate amplification reaction comprising a Stem primer having a mismatch, e.g., a mismatch at its 3' end ("mismatch Stem primer"); and the two reactions are simultaneously monitored and compared, wherein an incrase in the amplification rate of the site-specific Stem primer reaction relative to the mismatch Stem primer reaction is indicative of the presence of the site of interest in the amplicon (or concatmers thereof), and wherein it is indicative of the absence of the site of interest when the rate of the site-specific Stem primer reaction is the same or slower than the mismatch Stem primer reaction.

The region between the forward and reverse primer binding regions represents a region which is guaranteed to form part of the amplicon but does not itself conventionally provide for any primer binding sites. This region is referred to herein as the "stem region" of the amplicon. Primers which bind to the stem region are referred to herein as "stem primers." Stem primers can be defined as primers which bind to the stem region (FIG. 2). They may further be defined as primers that bind the region 3' of the forward primer binding region on the forward strand and 3' of the reverse primer binding site on the reverse strand. It is understood that the primer binding sites and the binding sites of the stem primers do not significantly overlap. It is preferred that the primer binding sites and the binding sites of the stem primers do not overlap at all.

"Significantly" in the context of overlapping primer binding regions means that the primer binding sites overlap by less than 10 nucleotides, less than 9 nucleotides, less than 8 nucleotides, less than 7 nucleotides, less than 6 nucleotides, less than 5 nucleotides, less than 4 nucleotides, less than 3 nucleotides, less than 2 nucleotides or less than 1 nucleotide. It is preferred that they do not overlap at all. Stem primers may further still be defined as primers that bind the region 3' of the forward primer binding region on the forward strand and 3' of the reverse primer binding site on the reverse strand but where the primer binding regions do not substantially overlap with any intra-molecular secondary structure generated as a direct consequence of the primers employed by a particular NAAT, especially a LFP.

The use of Stem primers significantly increases the rate of amplification. This has the distinct advantage that diagnostic tests, for example, can deliver test results in a shorter period of time, something of common value amongst users of diagnostic tests. An additional benefit of faster amplification is that it can decrease the possibility of false positive results and hence increase the specificity of a test. It has been observed that NAATs employing strand displacing polymerases become increasingly prone to non-specific amplification as the length of time required for amplification increases. As such, faster amplification can also lead to more accurate results. Therefore, the use of stem primers increases the rate of amplification of NAATs such as Loop-mediated Isothermal Amplification (LAMP), and provides greater flexibility in primer selection for a given target template.

Thus, in another embodiment, the described methods include the performance of an amplification technique based on the isothermal approach used in LAMP and LAMP-STEM. The general approach for loop-mediated isothermal amplification (LAMP) is illustrated in FIG. 1. Briefly, forward and reverse loop-forming primers (known as FIB and BIP primers) comprise, e.g., F1c and F2, B1c and B2, priming sites, respectively, on a target (single-stranded) nucleic acid template (FIG. 1a-b). The target nucleic acid can be from genomic DNA, cDNA, RNA. It is sometimes necessary to denature (via heat, ionic strength, or solvent conditions) double-stranded nucleic acid template to allow the primers to bind to the template.

In certain methods as described herein, a first-stage amplification (i.e., "pre-amp") reaction, e.g., LAMP reaction, is performed. The LAMP reaction, which includes, e.g., the loop-forming primers and one or more displacement primers proceeds at a relatively slow rate. The LAMP reaction results in the formation of a single stranded amplicon referred to as a "dumbbell" comprising a stem or middle region flanked by loops on the 3' end and 5' end created by the loop-forming primers (FIG. 1c). Further amplification cycles result in the production of concatamers of the "dumbbell" amplicons having alternating complementarity such that the loop-forming primers as well as the dumbbell structure drives additional rounds of extension.

In an exemplary amplification method as described herein, a first stage isothermal amplification reaction (i.e., "pre-amp step") using a NAAT, for example, a LAMP method is performed (i.e., FIG. 1a-c), which includes forward and reverse primers, FIP and BIP primers (comprising F1c and F2, B1c and B2, priming sites, respectively), and displacement primers (F3 and B3) to amplify a region on the target nucleic acid comprising one or more SNP sequences. The reaction mixture, which includes, e.g., the LAMP—generated amplicon, buffer and amplification reagents (e.g., dNTPs), and loop-forming primers can be utilized directly in the second stage of an exemplary amplification method as described herein.

In any of the embodiments described herein, the method further comprises the addition of at least one displacement or bumper primer in the first-stage and/or second-stage amplification reaction.

The method of synthesizing or amplifying nucleic acid according to the present invention is supported by the DNA polymerase catalyzing the strand displacement-type reaction for synthesis of complementary chain. During the reaction, a reaction step not necessarily requiring the strand displacement-type polymerase is also contained. However, for simplification of a constitutional reagent and in an economical viewpoint, it is advantageous to use one kind of DNA polymerase. As this kind of DNA polymerase, the following enzymes are known. Further, various mutants of these enzymes can be utilized in the present invention insofar as they have both the sequence-dependent activity for synthesis of complementary chain and the strand displacement activity. The mutants referred to herein include those having only a structure bringing about the catalytic activity required of the enzyme or those with modifications to catalytic activity, stability or thermostability by e.g. mutations in amino acids. Exemplary polymerases for use in the described methods include, Bst DNA polymerase, Bca (exo-)DNA polymerase, DNA polymerase I Klenow fragment, Vent DNA polymerase, Vent (exo-)DNA polymerase (Vent DNA polymerase deficient in exonuclease activity), Deep Vent DNA polymerase, Deep Vent(exo-)DNA polymerase (Deep Vent DNA polymerase deficient in exonuclease activity), .PHI.29 phage DNA polymerase, MS-2 phage DNA polymerase, Z-Taq DNA polymerase (Takara Shuzo Co., Ltd.), KOD DNA polymerase (Toyobo Co., Ltd.).

Among these enzymes, Bst DNA polymerase and Bca (exo-) DNA polymerase are particularly desired enzymes because they have a certain degree of thermostability and high catalytic activity. The reaction of this invention can be carried isothermally in a preferred embodiment, but because of the adjustment of melting temperature (Tm) etc., it is not always possible to utilize temperature conditions desired for the stability of the enzyme. Accordingly, it is one of the desired conditions that the enzyme is thermostable. Although the isothermal reaction is feasible, heat denaturation may be conducted to provide nucleic acid as a first template, and in this respect too, utilization of a thermostable enzyme broadens selection of assay protocol.

Vent (exo-) DNA polymerase is an enzyme having both strand displacement activity and a high degree of thermostability. It is known that the complementary chain synthetic reaction involving strand displacement by DNA polymerase is promoted by adding a single strand binding protein (Paul M. Lizardi et al., Nature Genetics, 19, 225-232, July, 1998). This action is applied to the present invention, and by adding the single strand binding protein, the effect of promoting the synthesis of complementary chain can be expected. For example, T4 gene 32 is effective as a single strand binding protein for Vent (exo-) DNA polymerase.

FIG. 2 illustrates an exemplary embodiment of the second-stage amplification reaction, a LAMP-STEM technique as described herein. In this example, the second-stage amplification reaction further comprises at least one site-specific primer (i.e., a site-specific Stem primer), which anneals or is complementary to a site-specific Stem primer-binding region or sequence in the amplicon from stage-one. In a preferred embodiment, the site-specific Stem primer has at its 3' end a nucleotide that is complementary to a nucleotide of interest (e.g., a SNP) in the amplicon from stage-one.

In certain embodiments, the methods include monitoring and comparing the rate of amplification in the second-stage reaction. If the site-specific Stem primer binding region in the amplicon from stage-one contains a nucleotide complementary to the 3' end of the site-specific Stem primer, the template will be amplified at an enhanced rate relative to a mismatch primer (i.e., a primer that binds to the same location as the site-specific Stem primer but that has a nucleotide at its 3' end that is not complementary to the amplicon). Because of the differential amplification rate between the SNP-Stem primer and a mismatch primer, it is possible to run both reactions in parallel and compare the rates. The more rapid appearance of amplification products in the site-specific Stem primer relative to the mismatch primer is indicative of the presence of the allele of interest.

The ability of loop-forming primers to generate stable, single stranded regions of amplicon is important to rapidly propagating further amplicon and represents a key aspect of technologies employing these primers. It means that concatameric amplicon can contain many new priming sites for the primers employed by the NAAT in question. In, e.g., LAMP, the loop-forming primers, which generate inverted repeats in the amplicon, also provide for single stranded regions of amplicon which they can themselves bind to and so initiate further re-copy of amplicon and hence further propagate amplification. In LAMP further additional primers may be used in addition to LFPs, which also bind to these single-stranded regions of amplicon to help further propagate amplification (known as loop primers). A facet of the present invention is that the stem primers do not bind to said stable single stranded loops generated by loop-forming primers and/or loop primers but accelerate amplification via a distinct mechanism.

Figure 3:
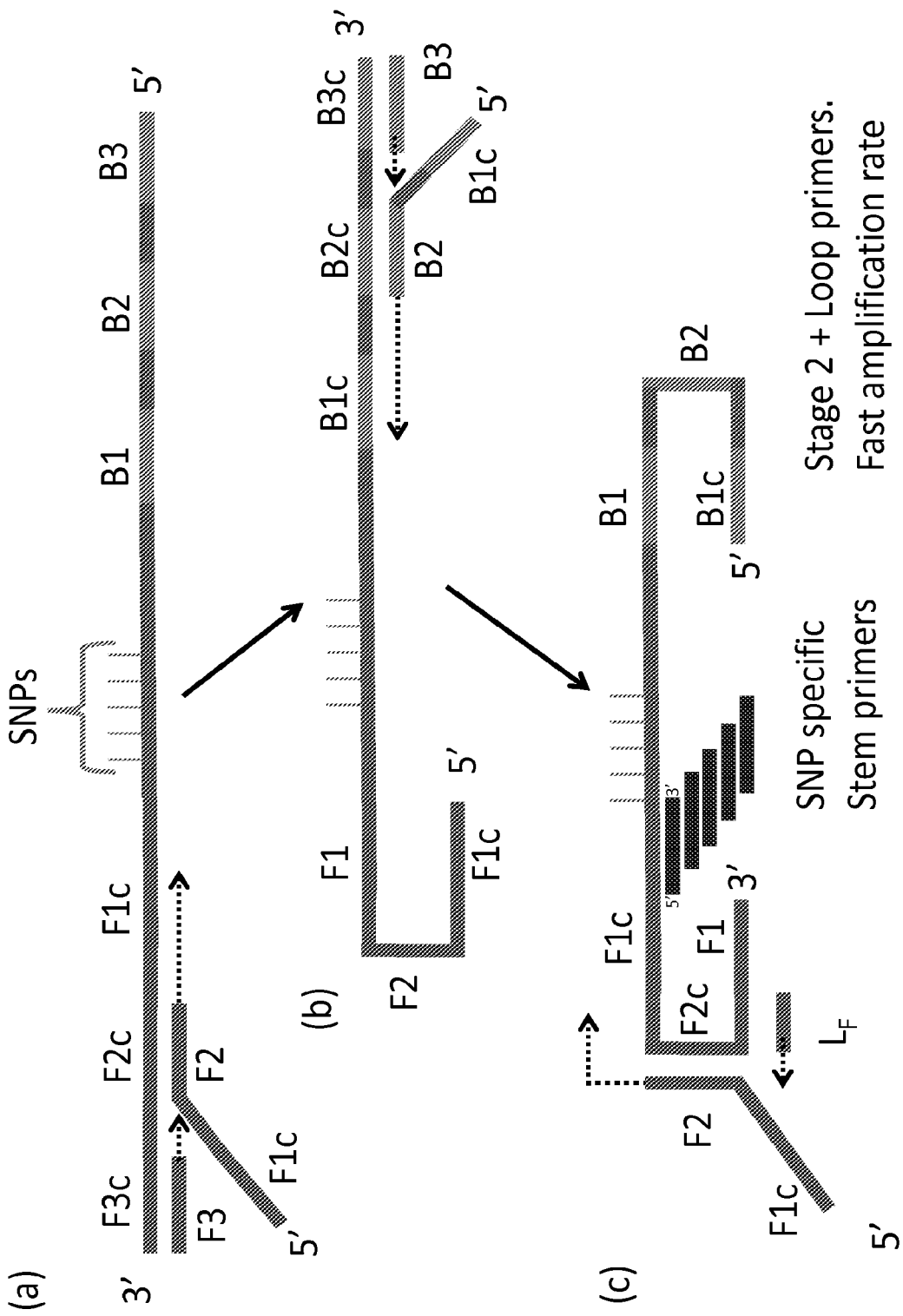
FIG. 3. Illustration of general principal for another exemplary modified LAMP-STEM technique as described herein. The technique is similar to that depicted in FIG. 2 but futher includes "Loop primers" in addition to the SNP-Stem primers. See WO0028082, incorporated herein by reference.

The LAMP-STEM component of the technique as described herein can further include additional primers, for example, "Loop primers" (FIG. 3) that anneal to regions within the loops generated by the Loop-forming primers. Loop pimers can further enhance the rate of the LAMP amplification reaction. In any of the embodiments described herein, the method further comprises the addition of at least one loop primer which is complementary to a region in the first loop or the second loop of the amplicon.

In any of the embodiments described herein, first-stage amplification reaction is preceeded by a heating step in which the target nucleic acid template and primers are heated to approximately 95° C. for from about 1 minute to about 30 mintues, including 2, 3, 4, 5, 6, 7, 8, 9, 10, 11, 12, 13, 14, 15, 16, 17, 18, 19, 20, 21, 22, 23, 24, 2,5 26, 27, 28, 29, 30, including all times in between. In certain embodiments, the target nucleic acid template and primers are heated to approximately 95° C. for from about 5 minutes to about 10 minutes.

In any of the embodiments described herein, the amplification reaction (i.e., first-stage and/or second stage) is performed at a temperature of from about 50° C. to about 80° C. In certain embodiments, the amplification reaction is performed at a temperature of about 55, 56, 57, 58, 59, 60, 61, 62, 63, 64, 65, 66, 67, 68, 69, 70, 71, 72, 73, 74, 75, 76, 77, 78, 79, 80° C. In certain embodiments, the amplification reaction is performed at a temperature of from about 55° to about 65° C.

In any of the embodiments described herein, the site-specific primer is in the forward direction. In certain embodiments, the site-specific primer is in the reverse direction. In still additional embodiments, both forward and reverse site-specific primers are included in the reaction.

In any of the embodiments described herein, a site-specific nucleotide is comprised at the 3' end of at least one of a loop-forming primer, a displacement primer, a site-specific primer, a loop primer or combination thereof.

In any of the embodiments described herein, the primers or nucleotide reagents comprise a chemical modification.

In accordance with the above, an exemplary two-stage isothermal nucleic acid amplification method for the detection of a site of interest comprises the steps of:

A) performing a first-stage nucleic acid amplification reaction comprising:
  1) providing a target nucleic acid template which comprises at least a first primer binding region, and a first and second loop-forming primer, wherein the target nucleic acid template defines a region of interest and comprises a site of interest;
  2) annealing a first loop-forming primer comprising a first and a second segment to the target template, wherein the first segment is substantially complementary to the first primer binding region on the template and the second segment comprises a sequence that is substantially complementary to another region in the first primer or a region in the amplicon generated from the first segment of the first loop-forming primer such that the second segment is able, under suitable conditions, to form a first single-stranded loop in the amplicon;
  3) extending the first loop-forming primer from its 3' end under suitable conditions with a polymerase having strand displacement activity, to form a single-stranded nucleic acid molecule, wherein the second segment of the first loop-forming primer hybridizes to a region in the amplicon generated from the first segment of the first loop-forming primer to form a first single-stranded loop having the 5' end of the first loop-forming primer;
  4) annealing to the amplicon from (3) a second loop-forming primer comprising a first and a second segment, wherein the first segment is substantially complementary to a second-loop forming primer binding region on the amplicon from (3), and the second segment comprises a sequence that is substantially complementary to another region in the second loop-forming primer or a region in the amplicon generated from the first segment of the second loop-forming primer such that the second region is able to form a second single-stranded loop in the amplicon;
  5) extending the second loop-forming primer from its 3' end under suitable conditions with a polymerase having strand displacement activity, to form a single-stranded nucleic acid molecule, wherein the second segment of the second loop-forming primer hybridizes to a region in the amplicon to form a second single-stranded loop having the 5' end of the second loop-forming primer;
  6) repeating steps A2-5, and thereby amplifying the nucleic acid template region between the two loop-forming primers comprising the site of interst, wherein a mixure is formed comprising the amplified nucleic acid (primary amplicon), and first and second loop-forming primers; and B) performing a second-stage amplification reaction comprising:
  1) providing the mixture from step A6, and separating into a plurality ofreactions, wherein, to at least one of thereactions, at least one site-specific Stem primer is included, which is substantially complementary to a site-specific primer binding region (site-specific region of interest) in the primary amplicon, and wherein at least one other reactionincludes no secondary primer;
  2) annealing the Stem primer, and the first and second loop-forming primers to theprimary amplicon, and extending them from their 3' ends under suitable conditions with a polymerase having strand displacement activity;
  3) repeating step B2, and thereby further amplifying the primary amplicon; and
  4) detecting and comparing in real-time the rate of amplification by the site-specific Stem primer and rate of amplification in the reaction with no secondary primer, wherein an increased rate of amplification by the site-specific Stem primer relative to other reaction is indicative of the presence of the site of interest in the amplified nucleic acid, and wherein a slower or similar rate is indicative of the absence of the site of interest in the amplified nucleic acid.

In certain embodiments, the second-stage amplification reaction proceeds at an increased rate relative to the first.

In certain embodiments, the plurality of reactions include approximately equal volumes or amounts of the primary amplicon from the first-stage amplification reaction.

In certain embodiments, step (B)(1) further comprises including to at least one additional reaction a mismatch Stem primer. In additional embodimetns, step (B)(4) comprises detecting and comparing in real-time the amplification rate of the site-specific primer reaction, the mismatch primer reaction, and the reaction with no secondary primer, wherein an increase in the amplification rate in the site-specific primer reaction relative to the others (as well as the first-stage reaction) is indicative of the presence of the site of interest.

As would be appreciated by those of skill in the art, in any of the aspects or embodimens as described herein, the methods can be modified so as to include any desired number of individual or discrete second-stage reactions, any number of which can include, respectively, no secondary primer, a site-specific primer or a mismatch primer. Indeed, the methods include configurations where the same or different site-specific primers and/or the same or different mismatch primers are run in parallel in separate reactions, and all are detected and compared simultaneously and in real-time.

Where the primers further contain a second segment, the second segment comprises a sequence that is substantially complementary to another segment in the first primer or a region in the amplicon generated from the first segment of the first primer such that the second region is able to form a loop. "An amplicon generated from the first segment of the first primer (or second primer)" refers to the first copy of the template which is generated when the first primer is extended by a polymerase. Said amplicon includes the sequence of the first primer at its 5' end.

In certain embodiments, the second segment is substantially identical to a region on the target template and/or the amplicon to which the primer binds. Such primers are referred to herein as loop-forming primers. "Substantially identical" means that the second segment has at least 70%, 80%, 90%, 95%, 99% or 100% identity to the region on the target template and/or the amplicon. It is also envisioned that only part of the second region shows substantial identity with a region on the target template. Regardless of whether the whole or only part of the second segment of the primer shows substantial identity with a region on the target template, the region of the second segment which is substantially identical to a region on the target template and/or amplicon is at least 5 nucleotides, at least 10 nucleotides, at least 20 nucleotides, at least 30 nucleotides, at least 40 nucleotides, at least 50 nucleotides, at least 60 nucleotides, or even at least 70 nucleotides in length. In this aspect of the invention, once the first segment of the primer has been extended to form a first amplicon, the second segment is able to bind to a complementary region within the same strand and thereby form a loop.

The methods of the invention may be practised using forward and reverse primers of the same kind, e.g. loop-forming primers (LFP), hairpin primers, etc. When referring to "the same kind of primers", it is meant that the primers are all simple primers, LFPs, LPPs or hairpin primers. The term "different kind of primers" accordingly relates to a combination of two or more primers wherein at least one of the primers is not of the same kind as the other primer(s). For example, where a method uses four primers of which three are LFPs and one is a LPP, the primers would be considered to be of a different kind. Thus, it is also envisioned to use forward and reverse primers which are not of the same kind. For example, a forward primer may be used that is a LFP in combination with a reverse primer that is a LPP or a hairpin primer. It is also possible to combine LFPs or hairpin primers with simple primers provided that the combination of primers results in the formation of a concatamer. Where the NAAT used for amplification employs more than one (i.e. two or more) forward and/or reverse primer, it is also possible to combine the same or different kinds of primers on the same primer binding site. In one aspect of the present invention, the two or more forward and/or reverse primers are all LFPs. Suitable combinations of primers will be evident to those of skill in the art. For example, it will be evident to the skilled person that the combination of forward and reverse primers that are all simple primers may not provide a mechanism to provide for the formation of a concatamer and therefore such a combination is not suitable for use in the present invention.

It is to be understood that, in general, the forward and reverse primers, or sets of primers, act on different strands of the target template. Furthermore, the primers (or one of each set of primers) will act to delimit the region of the original polynucleotide copied and recopied. Thus exponential amplification requires the coupling of activities between at least two primer binding regions, a forward primer binding region and a reverse primer binding region (FIG. 1). The forward and reverse primer binding regions may each comprise a single binding site for a primer whereby the sites are on opposite sense strands i.e. one primer binding site is on the "forward strand", one on the "reverse strand" (as shown in FIG. 1). The forward and reverse primer regions may also comprise binding sites for two or more primers each, where more than two primers are employed by a particular NAAT. In this case, it is possible that the two or more primer binding sites in the forward and/or reverse primer binding regions are all situated on the same strand of the target template and/or amplicon or on different strands of the target template and/or amplicon.

Stem primers as used in certain methods described herein may be positioned anywhere between the forward and reverse primer binding regions provided that the binding site(s) of the stem primer(s) do(es) not significantly overlap with the forward or reverse binding site. It is to be understood that in the case where a LFP is employed, where the LFP is a forward primer, the forward primer binding region encompasses not only the F2 site (i.e. the forward primer binding region) but also the F1 site (i.e. the region on the forward strand which is substantially identical to the second segment of the LFP), and where the LFP is a reverse primer, the reverse primer binding region encompasses not only the R2c site (i.e. the reverse primer binding region but also the R1c site (i.e. the region on the reverse strand which is substantially identical to the second segment of the LFP; FIG. 1). In this way the stem primers may be positioned anywhere between the R1(c) and F1(c) sites where two LFPs are employed (as in LAMP and TRA); where a single LFP is employed in a particular NAAT, the stem primers may bind between either a R1(c) or F1(c) site and another primer binding region occupied by a non-LFP.

It is possible to employ only one stem primer which binds either the forward or reverse polynucleotide strand (as shown in FIG. 2). Alternatively, two or more stem primers may be used which can bind either to strand of the amplicon or to the same strand. The methods of the present invention may be practised with one, two, three, four or more stem primers which can be used in any spatial combination and which may bind either the reverse or forward strand provided that the binding sites for the stem primers do not significantly overlap with the forward or reverse primer binding regions or do not overlap at all. The stem primers may further bind to any part within the stem region. Thus, the stem primer(s) may have a binding site which is in close proximity to the forward or reverse primer binding region.

"Close proximity" means that the binding region of the stem primer and the forward/reverse primer binding region are no more than 10 bp, 50 bp, 100 bp, 200 bp, 300 bp, 400 bp, 500 bp, 600 bp, 700 bp, 800 bp, 900 bp or 1000 bp apart.

In certain embodiments, the stem primers may be at least 5 nucleotides, at least 10 nucleotides, at least 20 nucleotides, at least 30 nucleotides, at least 40 nucleotides, at least 50 nucleotides, at least 60 nucleotides, at least 70 nucleotides, at least 80 nucleotides or at least 90 nucleotides in length. The stem primers may be simple primers. However, it is also envisioned to use stem primers that are LFPs, hairpin primers, LPPs, chimeric primers, or other derivatives. Where more than one stem primer is used, the stem primers may be of the same kind or may be a combination of different kinds of primers.

There is a great variety of possible combinations of "simple primers", LFPs, hairpin primers, RNA containing primers, nickase site containing primers and other novel primers which could be used in novel combinations to generate derivatives of the methods outlined in respective NAAT methods. Where said combinations result in methods which generate concatameric amplicon capable of self-copying to generate longer concatamers, stem primers are anticipated to be applicable.

In certain embodiments, the site-specific Stem primer comprises at its 3' end a nucleotide that is complementary to a nucleotide of interest in the amplified nucleic acid template or amplicon. In still additional embodiments, the mismatch Stem primer comprises a 3' end nucleotide that is not complementary to a nucleotide of interest in the amplified nucleic acid template or amplicon.

In certain additional embodiments, the complementary or site-specific Stem primers may decrease the time required to detect a particular type and amount of target template by at least 1 minute, at least 2 minutes, at least 3 minutes, at least 5 minutes, at least 10 minutes, at least 20 minutes, at least 30 minutes or at least 60 minutes compared to a control reaction to which no stem primer(s) or a mismatch stem primer has/have been added.

Stem primers act to increase the rate of amplification of methods employing LFPs via the coupling of processes occurring at the forward and reverse binding regions and since it has been taught in the literature that the LAMP method has an upper limit to the number of nucleotides separating the forward and reverse binding sites for the LFPs employed (Notomi et al. Loop-mediated isothermal amplification of DNA, Nucleic Acids Research, (2000) Vol 28., No. 12, e63), the use of stem primers can clearly allow the forward and reverse binding sites to be located further apart in the sequence than previously practicable (especially if several stem primers are employed). This can have great benefit when it is desirable to demonstrate that two regions of sequence occur together on a polynucleotide but where the distance between the two regions is too far to allow each respective region to be effectively used as a forward and reverse binding region in the NAATs described herein.

Since use of stem primers can allow for the forward and reverse binding regions to be much further apart than in their absence and still allow for effective amplification, the presence of two distinct sites on a polynucleotide can be established. Thus the invention provides a method for amplification of a polynucleic acid wherein the forward and reverse primer binding regions are located at a distance such that synthesis of a polynucleic acid can occur only in the presence of the stem primer(s). This distance can be defined experimentally by performing two separate NAATs in parallel wherein the NAATs, the reagents and the amplification conditions used are identical except that stem primer(s) are added to one reaction but not the other. Where synthesis of the polynucleic acid occurs only in the presence of the stem primer(s), the primer binding sites are considered to be located at a distance such that synthesis of a polynucleic acid can occur only in the presence of the stem primer(s).

The stem primers may contain exclusively naturally occurring nucleic acids. However, it is also envisioned to utilise primers that contain modified bases. Examples of such modified bases include, but are not limited to, N4-methylcytosine, inosine, ribocleotides, fluorescent bases, photolysable bases or universal bases. It is also envisioned to use nucleic acids that have been labelled with a moiety that allows the stem primer and/or the amplicon to which the labelled stem primer binds to be detected. For example, the nucleic acid may be fluorescently labelled. The stem primers may alternatively be labelled with capture moieties (e.g. biotin).

Importantly, the stem primers are not directly responsible for exponential amplification of the amplicon, which is mediated by the primers binding to the forward and reverse primer binding sites, but merely increase the rate of amplification. This is because the stem primers are considered to function on the amplification products of the other primers employed by a particular NAAT. Hence, stem primers function by increasing the amplification rate of the reaction mediated by the forward and reverse primers. This is shown in FIG. 2, where it can be seen that were the stem primer to prime and extend from the target template, the partial copy of the target template would contain only either the forward primer binding region or the reverse primer region, but not both. Therefore, the principal amplicon generated from a stem primer would not allow for reciprocal copying and hence would not contribute to exponential amplification of the target template. The same argument applies to stem primers copying a principal amplicon generated by other primers employed by a particular NAAT and similarly for first generation amplicons.

Also, stem primers are only anticipated to significantly increase the rate of amplification of a target template if the next generation amplicon (i.e. further copies of the first generation amplicon (and copies of these copies)) is concatameric in nature. The requirement for stem primers to work on concatamers follows from the requirement that for a particular polynucleic acid to contribute to exponential amplification it must contain regions capable of acting as the forward and reverse primer binding regions. Copying of a concatameric structure via a stem primer, can produce a polynucleotide copy which has both forward and reverse primer binding sites, whereas copying a non-concatameric structure does not. Thus, the use of stem primers will be beneficial for amplification methods that result in the formation of concatamers.

The methods as described herein are well-suited for use with isothermal nucleic acid amplification methods making them relatively easy to perform, efficient, robust and reproducible. An advantage of the described methods is that they allow for the rapid identification of a desired target nucleic acid (e.g., genetic mutation, SNP, pathogenic infection, etc.) in a sample, including a complex mixture. The rapid amplification necessarily means that less time is required to identify the presence or absence of a targeted genetic element, and therefore, the present methods provide a convenient means for point-of-care genetic detection and diagnosis.

The term "substantially complementary" means that the first segment has sufficient complementarity to bind to the primer binding region on the template and/or amplicon under conditions which are commonly used during NAATs. This requires that the first segment of the primer has at least 70%, 80%, 90%, 95%, 99% or 100% complementarity to the primer binding region on the template. The first segment of the primer may be at least 5 nucleotides, at least 10 nucleotides, at least 20 nucleotides, at least 30 nucleotides, at least 40 nucleotides, at least 50 nucleotides, at least 60 nucleotides, or even at least 70 nucleotides in length.

In any of the embodiments described herein, the first or second-stage primers can comprise an endonuclease restriction site, or recognition element for a nicking enzyme.

In any of the embodiments described herein, the amplification reaction can comprise a hairpin primer comprising a first and a second segment, wherein the first segment is substantially complementary to a primer binding region on a template and the second segment comprises a sequence that is substantially complementary to another region in the primer.

In any of the embodiments described herein, the amplification reaction can comprise a loop-providing primer, comprising a hairpin primer in which the inverted repeats are separated by a linker region.

In any of the embodiments described herein, the amplification reaction can comprise a chimeric primer.

Figure 4:
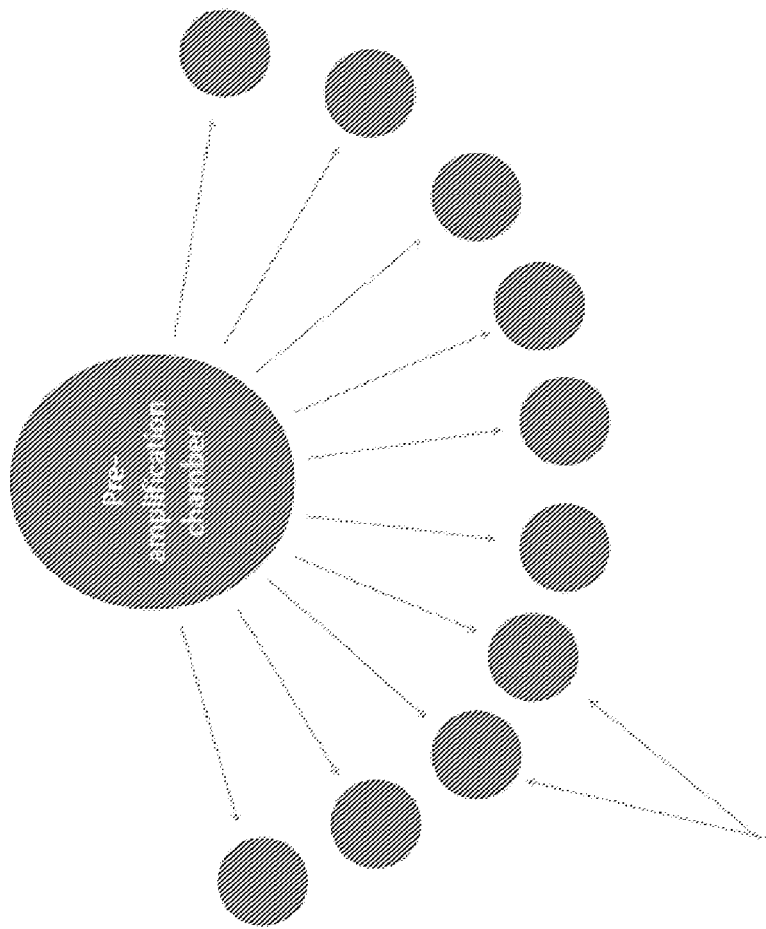
FIG. 4. Illustrates an exemplary system configured for performing the two-stage amplification method as described herein. In the example, the first-stage reaction is performed in a central chamber, which is in communication, e.g., fluid communication, with one or more additional chambers. In a preferred embodiment, the first-stage reaction mixture is distributed evenly to the one or more than one additional chambers where the second-stage amplification reaction takes place.

In any of the aspects or embodiments described herein, the first-stage amplification reaction may be performed in a container or chamber comprising a channel that is in fluid communication with one or more additional containers or chambers comprising primers for performing the second-stage amplification reaction (i.e., site-specific primer, site-specific Stem primer; mismatch primer, mismatch Stem primer, etc). In still additional embodiments, the first-stage reaction chamber comprises a channel that is in one-way fluid communication with one or more additional containers or chambers comprising primers for performing the second-stage amplification reaction. For example, as illustrated in FIG. 4 the first-stage reaction is performed in a central chamber that is in fluid communication with a plurality of additional chambers for performing the second-stage amplification reaction. In a preferred embodiment, the reaction mixture from the first-stage amplification reaction is automatically and simultaneously introduced into the additional chambers, which comprise the primers for performing the second-stage reaction.

In a preferred embodiment, an approximately equal amount or volume of the first-stage reaction mixture is automatically introduced from a central chamber to the axially arranged additional chambers via, e.g., centrifugal force. In certain embodiments, the method comprises performing a plurality of separate or discrete second-stage amplification reactions approximately simultaneously. In certain additional embodiments, the discrete reactions comprise the same or different site-specific primers. In still additional embodiments, the discrete reactions comprise a plurality or combination of site-specific primers (i.e., "multiplexing reaction").

In any of the aspects or embodiments described herein, each second-stage reaction volume can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 79, 80, 81, 82, 83, 84, 85, 86, 87, 88, 89, 90, 91, 92, 93, 94, 95, 96, 97, 98, 99, 100 µl or more. In a preferred embodiment, each respective second-stage reaction volume is 8 µl.

In certain embodiments, the description provides a method for detecting and comparing nucleic acid amplification comprising providing a first-stage reaction chamber; performing a first-stage pre-amplification reaction as described herein in the first-stage reaction chamber; introducing an amount or volume of the first-stage pre-amp reaction directly into a plurality of second-stage reaction chambers, wherein at least one second-stage reaction chamber comprises a site-specific primer, and at least one other second-stage reaction chamber comprises a mismatched primer; and performing in each second-stage reaction chamber a second-stage amplification reaction as described herein; and detecting and comparing in real-time the rate of amplification of each reaction simultaneously, wherein a faster rate of amplification in the site-specific primer reaction versus the mismatch primer reaction is indicative of the presence of the site of interest.

In any of the aspects or embodiments described herein, the first-stage amplification reaction can comprise site-specific primers such that the first-stage pre-amplification reaction is selective for a particular site of interest, and only if that site or region exists in the sample will rapid amplification of the template proceed at the second or later stage amplification reaction.

In any of the aspects or embodiments described herein, the second-stage (or later stage) amplification reaction can comprise multiple site-specific primers (i.e., "multiplex reaction"). By using differentially labeled site-specific oligonucleotides different amplification products can be detected and compared (i.e., multiplexed) within the same reaction.

Although several of the aspects and embodiments refer to a two-staged amplification scheme, the invention is not so limited. Indeed, the methods described herein are predicated upon the surprising discovery that the presence of a specific site or sequence of interest in a target nucleic acid region can be detected by the enhanced rate of amplification with a site-specific or sequence-specific (i.e., complementary) primer relative to the slower rate of an amplification reaction with mismatch primer that, but-for the mismatched base, anneals to the same target region. As such, any number of additional amplification steps can be performed, e.g., 3, 4, 5, 6, 7, 8, 9, etc., and therefore, any number of sites, regions or sequences of interest can be detected. Similarly, for each of the respective site-specific primer reactions to be performed, a parallel mismatch primer reaction can be performed and the rate of amplification of the two reactions monitored.

The skilled person will be aware that, in addition to the primers needed for amplification, the NAATs will require further reagents in order to synthesize a polynucleic acid. The required reagents will be evident to the person skilled in the art but will generally include a suitable buffer, dNTPs, a polymerase, etc.

As the skilled person will appreciate, following addition of all the necessary components for performing the NAAT in question, it is necessary to provide suitable conditions for the synthesis of the polynucleic acid. This can be achieved by providing a suitable incubation temperature, for example. It is preferred that amplification occurs under isothermal conditions. This means that during amplification the temperature is kept constant. "Constant" means that the temperature varies by no more than +/−10° C. However, methods that encompass a single temperature change of greater than 10° C., two temperature changes of greater than 10° C., three temperature changes greater than 10° C., four temperature changes greater than 10° C. or five temperature changes greater than 10° C. during the amplification process are also within the scope of the present invention.

In another aspect, the description provides a two-stage isothermal nucleic acid amplification and detection method comprising the steps of:
a. providing a LAMP amplified nucleic acid template comprising concatamerized amplicons, wherein the amplicons are formed of (i) a 3' end portion comprising a first region located 3' terminal that, under suitable conditions, anneals to a first complementary region to form a first loop; and (ii) a 5' end portion comprising a second region located 5' terminal that, under suitable conditions, anneals to a second complementary region to form a second loop;
b. admixing a portion of the nucleic acid template from (a) to: (i) a reaction mixture comprising at least one site-specific Stem primer that is substantially complementary to a site or region of interest between the first and second primer binding regions, wherein the site-specific primer includes at its 3' end a nucleotide that is complementary to a nucleotide of interest in the template, and (ii) a reaction mixture comprising no secondary primer;
c. annealing the primers from (b) to the nucleic acid template;
d. extending the primers from the 3' end under suitable isothermal conditions with a polymerase having strand displacement activity; and
e. repeating steps c-d, and thereby rapidly amplifying the nucleic template, and detecting and comparing in real-time the amplification rate of reaction (b)(i) with reaction (b)(ii), wherein an increase in the amplification rate in reaction (b)(i) relative to reaction (b)(ii) is indicative of the presence of the site of interest.

In certain embodiments, each reaction mixture includes approximately an equal volume or amount of the nucleic acid template.

In certain embodiments, step (b) further comprises admixing a portion of the nucleic acid template from (a) to (iii) a reaction mixture comprising a mismatch Stem primer. In additional embodimetns, step (e) comprises detecting and comparing in real-time the amplification rate of reactions (b)(i), (b)(ii), and (b)(iii), wherein an increase in the amplification rate in reaction (b)(i) relative to reaction (b)(ii) and (b)(iii) is indicative of the presence of the site of interest.

In any of the aspects or embodiments described herein, the method further comprises a step of detecting the formation of an amplicon in real-time. In certain embodiments, the amplification reaction mixture comprises fluorescently labeled dNTPs, a fluorescent DNA intercalating dye, chemiluminescent, electrochemical or other reporter system as a means to follow the extent of amplification in real-time. Thus, in certain embodiments, the formation of an amplicon is detected in real-time by measuring an increase in fluorescence. The amplification of the polynucleic acid according to the invention may be detected by methods known to those of skill in the art. Suitable methods include but are not limited to the use of fluorescent intercalating dyes, fluorescent primers or probes, measuring turbidity, electrochemical probes, bioluminescent signals and chemiluminescent probes.

The amplification of the polynucleic acid may be detected using real-time methods, i.e. methods that can detect the polynucleic acid as it is amplified. Examples of such detection systems include, but are not limited to, fluorescence (e.g. fluorescent probes that are added during the amplification), bioluminescent signals and electrochemical probes.

In one aspect, the primers themselves are labelled with a detectable moiety, e.g. a fluorescent label, a chemiluminescent label or an electrochemical label, that allows detection of the amplicon to which the primer(s) bind(s). Thus, a further utility of stem primers in concatamer forming NAATs could be as probe for use in a fluorescent, chemiluminescent or electrochemical reporter system as a means to follow the extent of amplification in real-time. Other suitable reporter systems will be evident to those of skill in the art. Stem primers could have benefit as probe containing primers over e.g. LFP or hairpin primers since they are not required to generate inverted repeats in amplicon which could affect certain types of probes. Alternatively, the amplification product may be detected using end-point measurements, i.e. measurements which take place after the amplification of the polynucleic acid has been completed.

The amplification of the polynucleic acid can also be detected by other detection methods employed in NAAT detection. Suitable examples include, but are not limited to, gene arrays, lateral flow strips, electrophoresis, mass spectroscopy and acoustic detection.

In one embodiment the Bioluminescent Assay in Real-Time (BART) reporter system is used to detect the synthesis of the polynucleic acid. This system has been explained in detail in WO2004/062338 and WO2006/010948, which are hereby incorporated by reference. BART is an example of a reporter system designed for isothermal NAATs which gives a single type of signal from a sample: a bioluminescent signal. BART utilizes the firefly luciferase-dependent detection of inorganic pyrophosphate: this is produced in large quantities when 'target' sequences are amplified using a NAAT. As such, molecular diagnostics can be achieved with BART simply by measuring the light emitted from closed tubes, in a homogeneous phase assay. BART is proven with several different NAATs, operating between 50-63° C. The BART reporter is a particularly effective means to follow the rate of amplification of a NAAT since the light output represents a measure of the instantaneous rate of amplification (whereas, e.g. fluorescent outputs show the accumulation of a signal and hence the measurements have to be differentiated to obtain the amplification rates).

BART being used in conjunction with LAMP to detect a dilution series of a particular target DNA molecule. Note that as the amount of target DNA in the sample decreases, the lag-phase to reach the time of maximal light increase (which is proportional to the lag-phase to reach maximal amplification) increases. Put differently, the time to reach the characteristic light peak associated with positive samples in BART increases in inverse proportion to the amount of target polynucleic acid in the sample. It is stressed that whilst the examples make use of the BART reporter system, the present invention is not limited to the use of BART and is equally applicable to methods such as fluorescence, turbidity, other spectroscopic techniques or electrochemical measurement methods irrespective of whether these are employed in real-time measurement of amplification or as end-point measurements.

Preferably, the method of the invention is performed in a sealed vessel. This is of great utility since it reduces or even prevents the possibility of the sample becoming contaminated. Moreover, it reduces or even prevents the possibility of the laboratory becoming contaminated. This is particularly important as if even one copy of the template polynucleic acid or amplicon were to escape into the laboratory, this could potentially contaminate other samples to be tested and give false-positive results. Thus, the ability to prevent contamination is of particular importance where a method of the invention is used in a diagnostic application.

In another aspect, the description provides methods for determining whether a particular polynucleic acid sequence is present in a nucleic acid sample or in organism's genetic code. For example, the methods can be used for determining whether the nucleic acid to which the template nucleic acid originates has been genetically modified, for detection of DNA associated with a particular non-genetically modified breed of plant or a genetically modified plant, for detection of DNA associated with pedigree breeds of animal or for medical or veterinary diagnostic applications such as genetic testing or forensic.

In any of the embodiments described herein, the target nucleic acid template can comprise genomic DNA, cDNA or RNA or a segment therefrom, from a virus, plant, microbe, fungus, mycoplasma, single cellular organism, or multicellular organism, e.g., a mammal, such as a human. In certain embodiments, the genomic DNA is from a pathogenic virus or microbe, e.g., bacteria or mycoplasma.

Thus, in another aspect, the description provides methods for diagnostic applications. In particular the methods allow identification and quantification of organisms in a patient and other samples. The methods of the present invention are also suitable for the detection of mutations, genetic diseases, or single-nucleotide polymorphisms (SNPs). The methods of the present invention are also suitable for the detection of pathogenic and non-pathogenic micro-organisms or viruses.

The organism may be any micro-organisms, such as viruses, bacteria, mycoplasma and fungi. The micro-organism can be pathogenic but it may also be a non-pathogenic micro-organism. The microorganism may also be a genetically modified organism (GMO). Furthermore, the methods of the present invention can be used to identify genetically modified crops and animals, for the detection of a disease state; for the prediction of an adverse reaction from a therapy and also for the prediction of a disease state susceptibility.

For example, in one embodiment, the description provides a two-stage method of detecting the presence of a nucleic acid of interest or diagnosing a disease. In certain embodiments, the method as described herein can be used for the real-time, rapid identification of a micro-organism, such as a virus, bacteria, mycoplasma, fungus, or a genetic disease, mutation, SNP, wherein said method comprises providing a nucleic acid sample from subject to be tested, e.g., a patient sample, performing the two-stage amplification reaction as described herein, and detecting and comparing in real-time the amplification rate of a site-specific primer amplification rate with a mismatch primer amplification rate, wherein an increase in the site-specific primer amplification rate relative to the mismatch primer amplification rate is indicative of the presence of the specific site, region or nucleotide(s) of interest, e.g., a site, region, or nucleotide(s) associated with at least one of a genetic disease, mutation, SNP, virus, or microbe, e.g., bacteria.

In certain embodiments, the microbe is a bacterium. In certain embodiments, the bacteria is a member of a genus selected from the group consisting of *Bacillus, Bartonella, Bordetella, Borrelia, Brucella, Campylobacter, Chlamydia, Chlamydophila, Clostridium, Corynebacterium, Enterococcus, Escherichia, Francisella, Haemophilus, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio*, and *Yershinia*.

In embodiments, the bacteria is a member of the group consisting of *Bacillus anthracis, Bacillus cereus, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumonia, Chlamydia trachomatis, Chlamydophila psittaci, Clostridium botulinum, Clostridium difficile, Clostridium perfringens, Clostridium tetani, Corynebacterium diphtheria, Enterococcus faecalis, Enterococcus faecium, Escherichia coli, Francisella tularensis, Haemophilus influenza, Helicobacter pylori, Legionella pneumophila, Leptospira inlerrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumonia, Neisseria gonorrhoeae, Neisseria meningitides, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus pneumonia, Streptococcus pyogenes, Treponema pallidum, Ureaplasma urealyticum, Vibrio cholera, Yersinia pestis, Yersinia enterocolitica*, and *Yersinia pseudotuberculosis*.

In certain embodiments, the target nucleic acid template is from *tubercle bacillus* (MTB or TB). In certain additional embodimetns, the target nucleic acid template is from the rpoB gene from MTB. In still further embodiments, the target nucleic acid template is rpoB13.5 F6.

In certain embodiments, the virus is a member of a family selected from the group consisting of Adenoviridae, Herpesviridae, Papillomaviridae, Polyomaviridae, Poxviridae, Hepadnaviridae, Parvoviridae, Astroviridae, Caliciviridae, Picornaviridae, Coronaviridae, Flaviviridae, Togaviridae, Hepeviridae, Retroviridae, Orthomyxoviridae, Arenaviridae, Bunyaviridae, Filoviridae, Paramyxoviridae, Rhabdoviridae, and Reoviridae.

In certain embodiments, the virus is a member selected from the group consisting of Adenovirus, Herpes simplex type 1, Herpes simplex type 2, Varicella-zoster virus, Epstein-Barr virus, Human cytomegalovirus, Human herpesvirus type 8, Human papillomavirus, BK virus, JC virus, Smallpox, Hepatitis B, Human bocavirus, Parvovirus B19, Human astrovirus, Norwalk virus, coxsackievirus, hepatitis A virus, poliovirus, rhinovirus, Severe acute respiratory syndrome virus, Hepatitis C virus, yellow fever virus, dengue virus, West Nile virus, Rubella virus, Hepatitis E virus, Human immunodeficiency virus (HIV), Influenza virus, Guanarito virus, Junin virus, Lassa virus, Machupo virus, Sabiá virus, Crimean-Congo hemorrhagic fever virus, Ebola virus, Marburg virus, Measles virus, Mumps virus, Parainfluenza virus, Respiratory syncytial virus, Human metapneumovirus, Hendra virus, Nipah virus, Rabies virus, Hepatitis D, Rotavirus, Orbivirus, Coltivirus, and Banna virus.

In a further aspect, there is provided a kit for use in a method according to the invention. Preferably such a kit comprises all the components necessary to practice a method as described herein, including paired site-specific and mismatch primers. In certain aspects the kit comprises the target polynucleic acid which is to be tested, and/or reagents for preparing the biological sample for inclusion in the methods as described herein.

A kit for use in a method according to the invention preferably comprises a polynucleic acid polymerase, the substrates for the nucleic acid polymerase and primers suitable for isothermal amplification of the target polynucleic acid, as described earlier. More preferably, the kit further comprises buffer reagents, such as a source of magnesium ions, or additives known in the art to improve the performance of a NAAT such as Betaine or additives known to improve the shelf-life of kit reagents such as trehelose or additives known to help preserve reagents such as sodium azide. Alternatively, a kit for use in a method according to the invention may comprise only some of these components and/or additional components. The sample and any other components that have been omitted from the kit may then be added to the kit during use.

Preferably, at least one of the components of the kit is lyophilized or is in another form which is suitable for storage in the kit. More preferably, all of the components of the kit are lyophilized or in one or more other forms suitable for storage. Such other forms include components to which stabilizing factors have been added and/or a refrigerated or frozen master mix that contains the components of the kit.

In another aspect, the description provides a method of treating or preventing a disease, comprising performing a two-stage nucleic acid amplification as described herein on a patient sample, and wherein if the patent tests positive for the presence of a site of interest associated with a disease or infection, treating or administering to the patient an effective amount of an appropriate therapeutic or bioactive agent, e.g., antibiotic, anti-cancer agent, anti-inflammatory, antimicrobial, antiviral, antifungal, antipsychotic, etc. The term "bioactive agent" is used to describe an agent with biological activity to assist in effecting an intended therapy, inhibition and/or prevention/prophylaxis. The terms "treat", "treating", and "treatment", etc., as used herein, refer to any action providing a benefit to a patient including the treatment of any disease state or condition.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Hemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barré syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alström syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia, familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronbl ad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysylhydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxi a, Stickler syndrome, stroke, androgen insensitivity syndrome, tetrahydrobiopterin deficiency, betathalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alström syndrome), Vrolik disease, Waardenburg syndrome, Warburg Sjo Fledelius Syndrome, Weissenbacher-Zweymüller syndrome, Wolf-Hirschhorn syndrome, Wolff Periodic disease, Weissenbacher-Zweymüller syndrome and Xeroderma pigmentosum, among others.

The term "cancer" refers to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "anti-cancer agent" is used to describe an anti-cancer agent. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CH1R-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, vairubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox,gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "antivirals" include, for example, nucleoside reverse transcriptase inhibitors (NRTI), other non-nucleoside reverse transcriptase inhibitors (i.e., those which are not representative of the present invention), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used include, for example, other NNRTI's (i.e., other than the NNRTI's according to the present invention) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3-(methoxycarbonyl)phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl]piperazine, 1-[3-(Ethylamino)-2-[pyridinyl]-4-[(5-hydroxy-2-indolyl) carbonyl]piperazine, 1-[(6-Formyl-2-indolyl)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyethiourea (LY-73497), L-697,639, L-697,593, L-697,661, 3-[2-(4,7-Difluorobenzoxazol-2-yl)ethyl}-5-ethyl-6-methyl (pyridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

Antimicrobial agents include, e.g., antibiotics. In certain embodiments, the anti-microbial is an anti-tuberculosis drug, e.g., pyrazinamide or benzamide, pretomanid, and bedaquiline, among others.

EXAMPLES

The contents of all references, patents, pending patent applications and published patents, cited throughout this application are hereby expressly incorporated by reference. The above described compositions and methods are further exemplified by reference to the Figures and accompanying description below.

Figure 6:
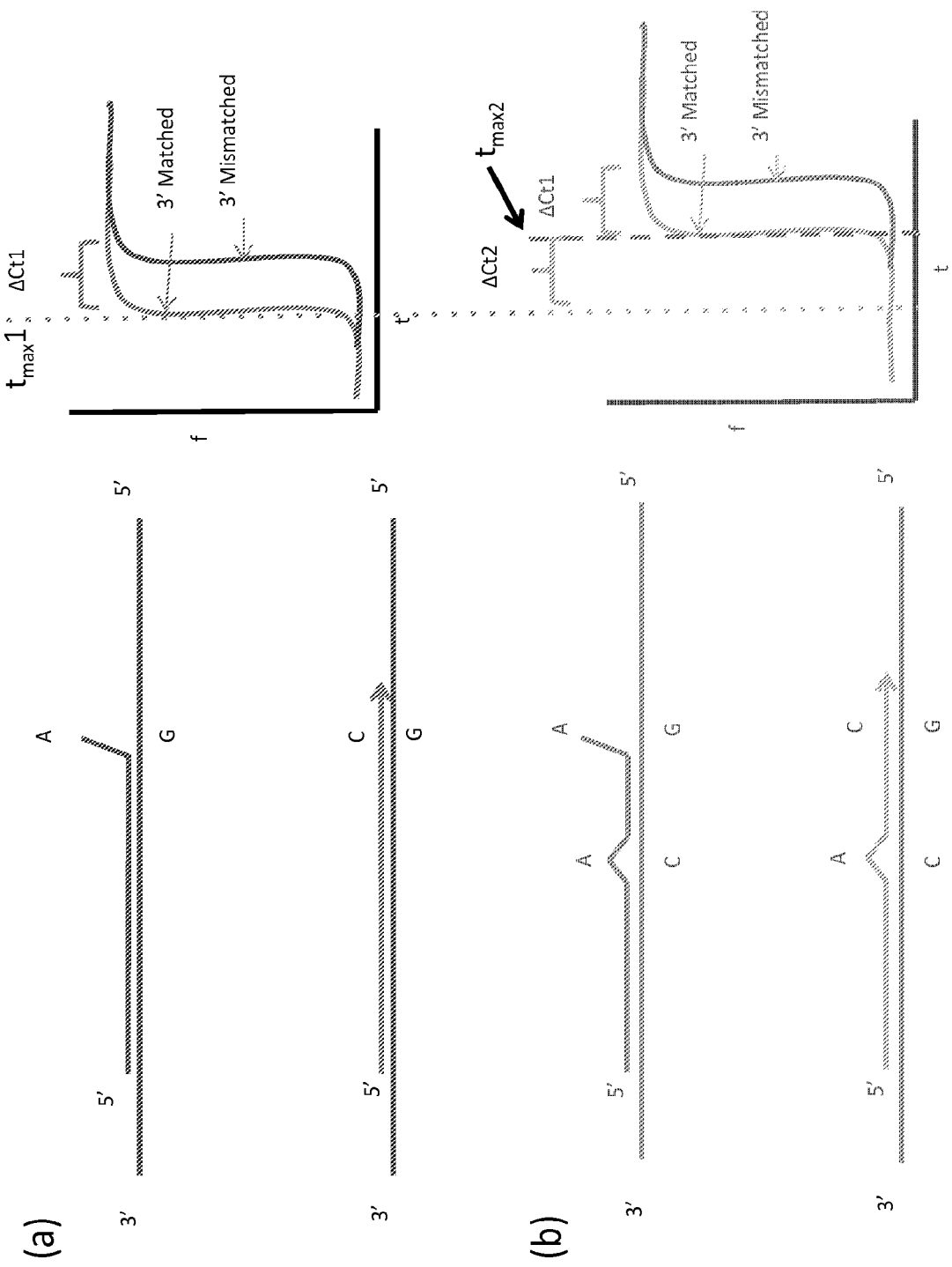
FIG. 6. Illlustrates the effect on rate of amplification due to mismatched bases in Stem primers. (a) The left panel exemplifies a Stem primer comprising a 3' end mismatch representing a primer that is not specific for a SNP of interest. The 3' mismatch induces a delay in the amplification reaction versus the matched or SNP-specific Stem primer ("SNP-Stem primer"). The increase in rate of amplification is exemplified in the right panel, wherein the dotted line represents the earliest time (t) to the point of maximum slope of fluorescence ($t_{max}1$), and $\Delta Ct1$ represents the lag in time to $t_{max}$ between the SNP-Stem primer and the 3' end mismatched Stem primer. (b) The right panel exemplifies another embodiment as described herein, wherein the Stem primers (SNP-Stem primer and 3' end mismatched primer) contain another base pair mismatch in their sequence. The second mismatch shifts to the right (i.e., reduces the rate) of amplification ($\Delta Ct2$) and delays the time to $t_{max}2$.

FIG. 6 illustrates the effect on rate of amplification due to mismatched bases in Stem primers. (a) The left panel exemplifies a Stem primer comprising a 3' end mismatch representing a primer that is not specific for a SNP of interest. The 3' mismatch induces a delay in the amplification reaction versus the matched or site-specific SNP Stem primer ("SNP-Stem primer"). The increase in rate of amplification is exemplified in the right panel, wherein the dotted line represents the earliest time (t) to the point of maximum slope of fluorescence ($t_{max}1$), and $\Delta Ct1$ represents the lag in time to $t_{max}$ between the SNP-Stem primer and the 3' end mismatched Stem primer. (b) The right panel exemplifies another embodiment as described herein, wherein the Stem primers (SNP-Stem primer and 3' end mismatched primer) contain another base pair mismatch in their sequence. The second mismatch shifts to the right (i.e., reduces the rate) of amplification ($\Delta Ct2$) and delays the time to $t_{max}2$.

Figure 7:
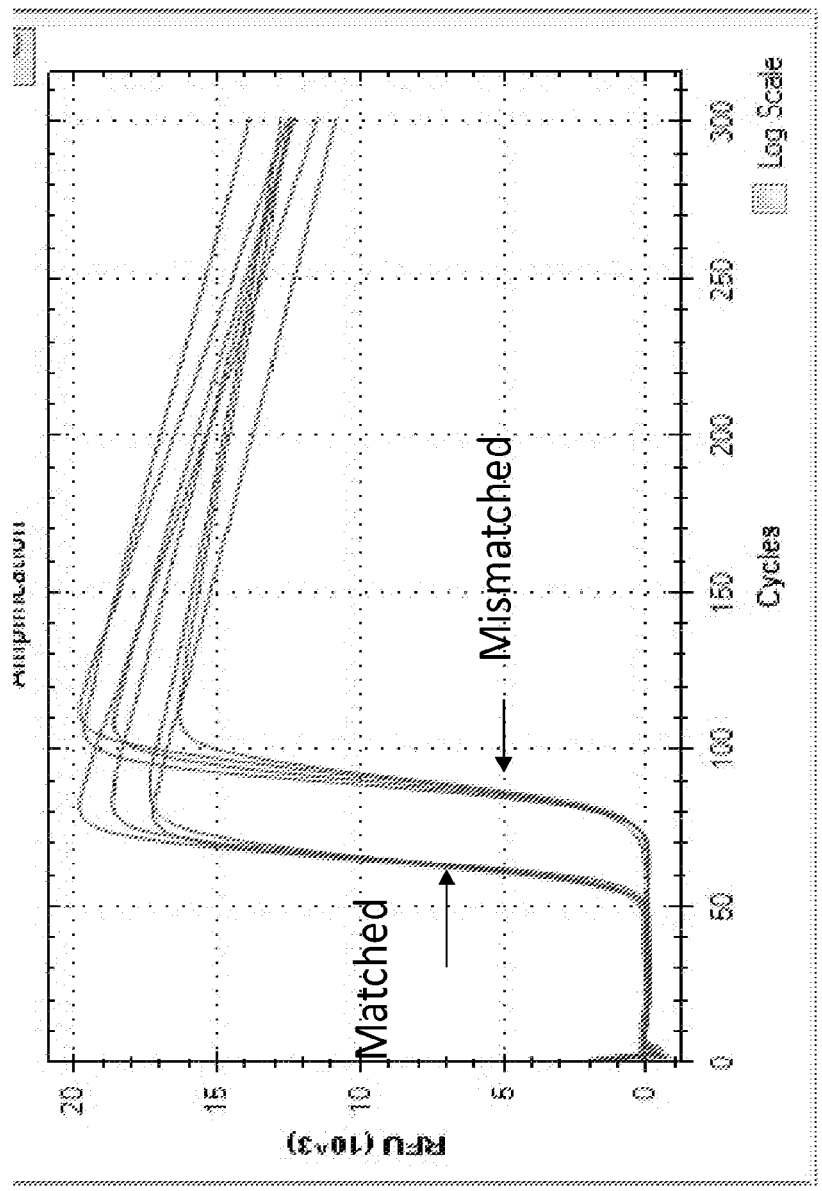
FIG. 7. Processed fluorescent traces showing matched Stem primer (i.e., SNP-Stem primer) LAMP reactions (n=4), and mismatched Stem primer LAMP reactions (n=4) using the Bio-Rad CFX realtime PCR instrument.

FIG. 7 processed fluorescent traces showing matched Stem primer (i.e., SNP-Stem primer) LAMP reactions (n=4), and mismatched Stem primer LAMP reactions (n=4) using the Bio-Rad CFX real-time PR instrument. The reaction was held at 65° C. and each cycle consisted of a fluorescent measurement every 15 seconds. The reaction was assembled on ice in a 48 well microplate. The solution consisted of about 200 copies of MTB genomic DNA per reaction, 20 mM Tries pH 8.8, 10 mM ammonium sulfate, 50 mM KCl, and 2.0 mM magnesium sulfate, 0.1% NP-40, 1× EVAgreen dye, Bst DNA polymerase and 1.4 mM dNTPs.

Figure 8:
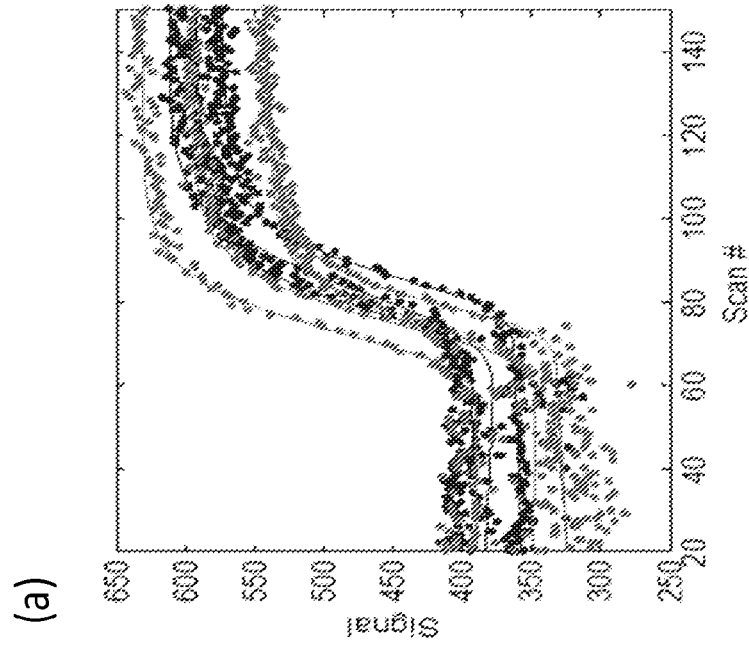
FIG. 8. Illustrates the enhanced rate of amplification observed according to an exemplary method as described herein. (a) Provides raw traces showing matched Stem primer (i.e., SNP-STEM) reactions (light traces) and mismatched Stem primer reactions (dark traces). (b) Quantification cycle (Cq; See Hellemans et al., 2007) is measured from the fitted raw traces as the point of maximum slope. The Cq for matched primers is plotted (light dots) along with mismatched Stem primers (dark dots) and no Stem primer LAMP ("dumbbell") reactions (open circles).

FIG. 8 illustrates the enhanced rate of amplification observed according to an exemplary method as described herein. (a) Provides raw traces showing matched Stem primer reactions for site-specific Stem primer reactions (light traces) and mismatched Stem primer reactions (dark traces). (b) Quantification cycle (Cq; See Hellemans et al., 2007) is measured from the fitted raw traces as the point of maximum slope. The Cq for matched primers is plotted (light dots) along with mismatched Stem primers (dark dots) and no Stem primer LAMP ("dumbbell") reactions (open circles). The cocktail for the first LAMP reaction (performed in a first chamber) contained about 200 copies of MTB genomic DNA in a solution of AMP buffer (20 mM Tris pH 8.8, 10 mM ammonium sulfate, 50 mM KCl, and 3.4 mM magnesium sulfate, 0.1% NP-40, 1× EVAgreen dye, Bst DNA polymerase and 1.4 mM dNTPs). The solution was introduced into a first chamber at 65° C., and incubated for 5 minutes before being distributed directly, automatically, and simultaneously into to a number of second reaction chambers. LAMP primers to the rpoB gene were dried in the first reaction chamber and supported LAMP amplification.

Accelerating Stem primers were dried in the second reaction chamber and were either perfectly matched (representing a SNP-Stem primer) or mismatched at the 3' end to the D435 drug resistance mutation of the MTB rpoB gene. As a negative control, several second reaction chambers contained no Stem primers and demonstrated no accelerated amplification. Amplification in the second reaction chamber was detected by directly measuring the increase in fluorescence caused by intercalation of EVAgreen dye into double-stranded amplified DNA. The fluorescence reaction was monitored continuously for 150 cycles of 15 seconds duration.

TABLE 1 rpoB STEM-LAMP Test.

| | | Matched Stem Cq | Mismatched Stem Cq | Dumbbell Cq | Δ(mismatched-matched Stem) | Δ(dumbbell-matched Stem) |
|---|---|---|---|---|---|---|
| rpoB13.5 F6 pre-amp | Unit 2 | 38.5 ± 13.5% (33~45) | 66.8 ± 9.6% (59~72) | 72.3 ± 16.6% (49~96) | 14 (24% acc.) | 4 (8% acc.) |
| | Unit 3 | 57.5 ± 9.1% (50~62) | 76.5 ± 1.3% (75~77) | 79.7 ± 5.6% (68~86) | 13 (17% acc.) | 6 (9% acc.) |

Exemplary Embodiments

In an embodiment, the description provides a two-stage nucleic acid amplification and real-time detection method comprising: a. providing a composition comprising a target nucleic acid template and at least one primer that anneals to the target nucleic acid template near a region of interest to be amplified; b. performing a first nucleic acid amplification reaction to amplify the region of interest, thereby forming aprimary amplicon; c. dividing (b) into at least twosecondary reactions, and including in at least one of the reactions a site-specific secondary primer that is complementary to a site-specific primer binding site that may be present within the primary amplicon and defines a site of interest within the region of interest; d. performing a second nucleic acid amplification reaction (second-stage reaction) thereby accelerating the amplification of the region of interest only if the site-specific primer binding site is complementary to the site-specific primer; and e. detecting and comparing in real-time the amplification rates of the at least two secondary reactions, wherein an enhanced relative rate of amplification in the reaction with the secondary primer indicates the presence of the sitee of interest that is complementary to the secondary primer.

In any of the embodiments described herein, step (a) includes a forward and reverse loop-forming primer. In any of the embodiments described herein, step (a) includes a forward and reverse displacement primer.

In any of the embodiments described herein, first nucleic acid amplification is an isothermal nucleic acid amplification reaction. In any of the embodiments described herein, the second nucleic acid amplification is an isothermal nucleic acid amplification reaction.

In any of the embodiments described herein, the first and/or second isothermal nucleic acid amplification reactions is LAMP or LAMP-STEM.

In any of the embodiments described herein, the primary amplicon is a concatamer.

In any of the embodiments described herein, the site-specific primer comprises a 3' end nucleotide complementary to a mutation, single nucleotide polymorphism (SNP), allele or biomarker on the amplicon.

In any of the embodiments described herein, the method comprises dividing (b) into at least an additional secondary reaction, wherein the additional secondary reaction includes a mismatch secondary primer. In any of the embodiments described herein, the mismatch primer comprises a 3' end nucleotide mismatch or 3' end nucleotide complementary to an allele, mutation or polymorphism different from the site-specific primer.

In any of the embodiments described herein, step (e) comprises detecting and comparing in real-time the amplification rates of all secondary rections, wherein an enhanced relative rate of amplification as compared to the other two reactions indicates the presence of the site of interest that is complementary to the secondary primer.

In any of the embodiments described herein, the mutation, SNP, or biomarker is specific for a genetic disease, a microbe or a virus.

In any of the embodiments described herein, the step of performing the second nucleic acid amplification reaction includes amplification in the presence of a fluorescent label or dye, thereby labeling the amplification products. In any of the embodiments described herein, the step of detecting and comparing in real-time the amplification rates includes detecting and comparing a fluorescent signal from each of the reactions.

In any of the embodiments described herein, prior to the first amplification reaction, the primer and template are heated to a temperature of approximately 95° C. for from about 1 minute to about 15 minutes. In any of the embodiments described herein, the first and second amplification reactions are performed at a temperature of from about 55° C. to about 65° C.

In any of the methods described herein, the first amplification reaction is performed in a first reaction chamber including a channel that is in one-way fluid communication with a plurality of second reaction chambers, and wherein step (c) includes transporting approximately equal volumes of (b) through the channels from the first reaction chamber to the second reaction chambers.

In any of the embodiments described herein, the method of claim 1, wherein the relative reaction rates of the amplification reactions satisfy the following condition: Second-stage amplification reaction+site-specific primer>>first-stage amplification reaction+mismatch primer>≈first-stage amplification reaction.

In any of the embodiments described herein, the method of claim 1, wherein the Cq of the second-stage site-specific or complementary primer amplification reaction is at least 25% faster than the second-stage mismatch primer amplification reaction.

In another embodiment, the description also provides a two-stage isothermal nucleic acid amplification method for diagnosing or detecting a disease or infection method comprising: a. providing a composition comprising a nucleic acid sample from a patient, and at least one primer that anneals to a target nucleic acid template near a region of interest to be amplified; b. performing a first isothermal nucleic acid amplification reaction to amplify the region of interest, thereby forming a primary amplicon; c. dividing (b) into at least tworeactions, and including to at least one of the reactions a site-specific secondary primer that is complementary to a site-specific primer binding region that may be present on the primary amplicon and defines a site of interest that is indicative of a disease or infection; d. performing a second isothermal nucleic acid amplification reaction thereby amplifying the region of interest; e. detecting and comparing in real-time the amplification rate of thesecondary reactions, wherein an enhanced rate of amplification in the site-specific secondary primer reaction relative to the other is indicative of the presence of the site of interest; and f. diagnosing the patient as having or not having a disease or infection corresponding to the site of interest.

In any of the embodiments described herein, the target nucleic acid template is from a microbe or virus. In any of the embodiments described herein, the target nucleic acid template is from *tubercle bacillus* (MTB or TB).

In any of the embodimetns described herein, the site of interest is in the rpoB gene. In any of the embodiments described herein, the site of interest is a SNP in the rpoB gene.

In any of the embodiments described herein, the method comprises the step of treating the patient testing positive for the site of interest by administering an effective amount of an appropriate therapeutic to treat the disease or infection. In any of the embodiments described herein, the therapeutic is an anti-tuberculosis therapeutic.

In another embodiment, the description provides a two-stage nucleic acid amplification and real-time detection method comprising: a. providing a composition comprising a target nucleic acid template and at least one primer that anneals to the target nucleic acid template near a region of interest to be amplified; b. performing a first nucleic acid amplification reaction to amplify the region of interest, thereby forming a primary amplicon; c. dividing (b) into at least three secondary reactions, and including in at least one of the reactions a site-specific secondary primer that is complementary to a site-specific primer binding site that may be present within the primary amplicon and defines a site of interest within the region of interest, and including in at least another of the reactions a mismatch secondary primer that anneals at or near the site of interest but is not complementary to the site of interest; d. performing a second nucleic acid amplification reaction (second-stage reaction) thereby accelerating the amplification of the region of interest only if the secondary primer binding site is complementary to the site-specific primer; and e. detecting and comparing in real-time the amplification rates of the secondary reactions, wherein an enhanced relative rate of amplification in the reaction with the site-specific secondary primer indicates the presence of the site of interest that is complementary to the site-specific secondary primer.

In any of the embodiments described herein, the method comprises dividing (b) into at least an additional secondary reaction, wherein the additional secondary reaction includes a mismatch secondary primer. In any of the embodiments described herein, the mismatch primer comprises a 3' end nucleotide mismatch or 3' end nucleotide complementary to an allele, mutation or polymorphism different from the site-specific primer.

In any of the embodiments described herein, step (e) comprises detecting and comparing in real-time the amplification rates of all secondary rections, wherein an enhanced relative rate of amplification as compared to the other two reactions indicates the presence of the site of interest that is complementary to the secondary primer.

In any of the embodiments described herein, the method comprises dividing (b) into at least one additional secondary reaction including a second site-specific secondary primer complementary to a second site-of interest that may be present within the primary amplicon and defines a second site of interest within the region of interest. Those skilled in the art will recognize, or be able to ascertain using no more than routine experimentation, many equivalents to the specific embodiments of the invention described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

REFERENCES

The following references are incorporated herein by reference in their entirety for all purposes.
1. Notomi T, Okayama H, Masubuchi H, Yonekawa T, Watanabe K, Amino N, Hase T (2000). "Loop-mediated isothermal amplification of DNA". Nucleic Acids Res. 28 (12): E63. doi:10.1093/nar/28.12.e63. PMC 102748. PMID 10871386.
2. U.S. Pat. No. 6,410,278, Notomi T, Hase T, "Process for synthesizing nucleic acid", published 2002 Jun. 25, assigned to Eiken Kagaku Kabushiki Kaisha
3. Nagamine K, Hase T, Notomi T (2002). "Accelerated reaction by loop-mediated isothermal amplification using loop primers". Mol. Cell. Probes 16 (3): 223-9. doi: 10.1006/mcpr.2002.0415. PMID 12144774.
4. Mori Y, Nagamine K, Tomita N, Notomi T (2001). "Detection of loop-mediated isothermal amplification reaction by turbidity derived from magnesium pyrophosphate formation". Biochem. Biophys. Res. Commun. 289 (1): 150-4. doi:10.1006/bbrc.2001.5921. PMID 11708792.
5. Mori Y, Kitao M, Tomita N, Notomi T (2004). "Real-time turbidimetry of LAMP reaction for quantifying template DNA". J. Biochem. Biophys. Methods 59 (2): 145-57. doi:10.1016/j.jbbm.2003.12.005. PMID 15163526.
6. Njiru Z K, Mikosza A S, Armstrong T, Enyaru J C, Ndung'u JM, Thompson A R (2008). "Loop-mediated isothermal amplification (LAMP) method for rapid detection of Trypanosoma brucei rhodesiense". PLoS Negl Trop Dis 2 (1): e147. doi:10.1371/journal.pntd.0000147. PMC 2238707. PMID 18253475. open access publication—free to read
7. Tomita N, Mori Y, Kanda H, Notomi T (2008). "Loop-mediated isothermal amplification (LAMP) of gene sequences and simple visual detection of products". Nat Protoc 3 (5): 877-82. doi:10.1038/nprot.2008.57. PMID 18451795.
8. Sen K, Ashbolt N J (2011). Environmental microbiology: current technology and water application. Norfolk, UK: Caister Academic Press. ISBN 978-1-904455-70-7.
9. Macarthur G (2009). Global health diagnostics: research, development and regulation. Academy of Medical Sciences Workshop Report (PDF). Academy of Medical Sciences (Great Britain). ISBN 978-1-903401-20-0.
10. Geojith G, Dhanasekaran S, Chandran S P, Kenneth J (2011). "Efficacy of loop mediated isothermal amplification (LAMP) assay for the laboratory identification of Mycobacterium tuberculosis isolates in a resource limited setting". J. Microbiol. Methods 84 (1): 71-3. doi:10.1016/j.mimet.2010.10.015. PMID 21047534.
11. Poon L L, Wong B W, Ma E H, Chan K H, Chow L M, Abeyewickreme W, Tangpukdee N, Yuen K Y, Guan Y, Looareesuwan S, Peiris J S (2006). "Sensitive and inexpensive molecular test for falciparum malaria: detecting Plasmodium falciparum DNA directly from heat-treated blood by loop-mediated isothermal amplification". Clin. Chem. 52 (2): 303-6. doi:10.1373/clinchem.2005.057901. PMID 16339303.
12. Njiru Z K, Mikosza A S, Matovu E, Enyaru J C, Ourna J O, Kibona S N, Thompson R C, Ndung'u J M (2008). "African trypanosomiasis: sensitive and rapid detection of the sub-genus Trypanozoon by loop-mediated isothermal amplification (LAMP) of parasite DNA". Int. J. Parasitol. 38 (5): 589-99. doi:10.1016/j.ijpara.2007.09.006. PMID 17991469.
13. Curtis K A, Rudolph D L, Owen S M (2008). "Rapid detection of HIV-1 by reverse-transcription, loop-mediated isothermal amplification (RT-LAMP)". J. Virol. Methods 151 (2): 264-70. doi:10.1016/j.jviromet.2008.04.011. PMID 18524393.
14. Sattabongkot J, Tsuboi T, Han E T, Bantuchai S, Buates S (2014). "Loop-mediated isothermal amplification assay for rapid diagnosis of malaria infections in an area of endemicity in Thailand". J. Clin. Microbiol. 52 (5): 1471-7. doi:10.1128/JCM.03313-13. PMID 24574279.
15. Francois P, Tangomo M, Hibbs J, Bonetti E J, Boehme C C, Notomi T. Perkins M D, Schrenzel J (2011). "Robustness of a loop-mediated isothermal amplification reaction for diagnostic applications". FEMS Immunol. Med. Microbiol. 62 (1): 41-8. doi:10.1111/j.1574-695X.2011.00785.x. PMID 21276085.
16. Torres C, Vitalis E A, Baker B R, Gardner S N, Torres M W, Dzenitis J M (2011). "LAVA: an open-source approach to designing LAMP (loop-mediated isothermal amplification) DNA signatures". BMC Bioinformatics 12: 240. doi:10.1186/1471-2105-12-240. PMC 3213686. PMID 21679460. open access publication—free to read
17. Iseki H, Alhassan A, Ohta N, Thekisoe O M, Yokoyama N, Inoue N, Nambota A, Yasuda J, Igarashi I (2007). "Development of a multiplex loop-mediated isothermal amplification (mLAMP) method for the simultaneous detection of bovine Babesia parasites". J. Microbiol. Methods 71 (3): 281-7. doi:10.1016/j.mimet.2007.09.019. PM1D 18029039.
18. Tanner N A, Zhang Y, Evans T C (2012). "Simultaneous multiple target detection in real-time loop-mediated isothermal amplification". BioTechniques 53 (2): 81-9. doi: 10.2144/0000113902. PMID 23030060.
19. US Patent Publication 2012/0157326.
20. U.S. Pat. No. 5,648,211.
21. Gandelman et al., Loop-Mediated Amplification Accelerated by Stem Primers. Int. J. Mol. Sci. 2011; 12(12): 9108-9124.

The invention claimed is:

1. A two-stage multiplexed nucleic acid amplification and real-time detection method comprising a. providing a composition comprising a target nucleic acid template and a combination of site-specific primers that anneal to the target nucleic acid template near a region of interest to be amplified; b. performing a first isothermal reaction to amplify the region of interest, thereby forming a primary amplicon; c. dividing (b) into at least two secondary reactions, and including in at least one of the reactions one or more site-specific secondary primer that is complementary to a site-specific primer binding site that may be present within the primary amplicon and defines a site of interest within the region of interest; d. performing a second isothermal reaction (second-stage reaction) thereby accelerating the amplification of the region of interest only if the site-specific primer binding site is complementary to the site-specific primer; and e. detecting and comparing the amplification rates of the at least two secondary reactions, wherein an enhanced relative rate of amplification in the reaction with the secondary primer indicates the presence of the site of interest that is complementary to the secondary primer.

2. The method of claim 1, wherein in step e), the detecting and comparing is in real time.

3. The method of claim 2, wherein the amplification reaction mixture comprises fluorescently labeled dNTPs, a fluorescent DNA intercalating dye, bioluminescent, chemiluminescent, electrochemical or other reporter system as a means to follow the extent of amplification in real-time.

4. The method of claim 1, wherein the isothermal nucleic acid amplification method is selected from Nucleic Acid Sequence Based Amplification (NASBA), Transcription Mediated Amplification (TMA), Helicase Dependent Amplification (HDA), Recombinase polymerase amplification (RPA), Strand Displacement Amplification (SDA), Loop-mediated Isothermal Amplification (LAMP), Chimera Displacement Reaction (RDC), Isothermal
 Chimeric Amplification of Nucleic Acids (ICAN), SMart Amplification Process (SMAP), Linear Isothermal Multimerization Amplification (LIMA), or Self Extending Amplification (SEA).

5. The method of claim 1, wherein the first nucleic acid amplification is Loop-mediated Isothermal Amplification (LAMP).

6. The method of claim 1, wherein step (a) includes a forward and reverse loop-forming primer.

7. The method of claim 6, wherein step (a) includes a forward and reverse displacement primer.

8. The method of claim 1, wherein the second isothermal nucleic acid amplification reaction is LAMP-STEM.

9. The method of claim 1, wherein the primary amplicon is a concatamer.

10. The method of claim 1, wherein the site-specific primer comprises a 3' end nucleotide complementary to a mutation, single nucleotide polymorphism (SNP), allele or biomarker on the amplicon.

11. The method of claim 1, wherein the method comprises dividing (b) into at least an additional secondary reaction, wherein the additional secondary reaction includes a mismatch secondary primer.

12. The method of claim 11, wherein the mismatch primer comprises a 3' end nucleotide mismatch or 3' end nucleotide complementary to an allele, mutation or polymorphism different from the site-specific primer.

13. The method of claim 1, wherein step (e) comprises detecting and comparing in real-time the amplification rates of all secondary reactions, wherein an enhanced relative rate of amplification as compared to the other two reactions indicates the presence of the site of interest that is complementary to the secondary primer.

14. The method of claim 2, wherein the mutation, SNP, or biomarker is specific for a genetic disease, a microbe or a virus.

15. The method of claim 1, wherein the step of performing the second nucleic acid amplification reaction includes amplification in the presence of a fluorescent label or dye, thereby labeling the amplification products.

16. The method of claim 15, wherein the step of detecting and comparing in real-time the amplification rates includes detecting and comparing a fluorescent signal from each of the reactions.

17. The method of claim 1, wherein a slow-rate isothermal pre-amplification is performed in the first-stage followed by multiple, discrete second-stage amplification and detection reactions performed in parallel directly on the products from the first-stage primary amplicon amplification product.

18. The method of claim 1, wherein the first-stage amplification reaction comprises site-specific primers such that a first-stage pre-amplification reaction is selective for a particular site of interest, and only if that site or region exists in the sample will rapid amplification of the template proceed at the second stage amplification reaction.

19. The method of claim 1, wherein the second-stage amplification reaction comprises multiple site-specific primers.

20. The method of claim 1, wherein an amount or volume of the first-stage reaction is introduced directly into a plurality of second reaction chambers.

21. The method of claim 1, further comprising the steps of providing a first reaction chamber; performing a first-stage pre-amplification reaction in the first reaction chamber; introducing an amount or volume of the first-stage pre-amp reaction directly into a plurality of second reaction chambers, wherein at least one second reaction chamber comprises a site-specific primer, and at least one second reaction chamber comprises a mismatched primer; and performing in each second reaction chamber a second-stage amplification reaction.

22. The method of claim 1, wherein the first-stage and second-stage amplification reactions are performed sequentially in the same reaction container or chamber.

23. The method of claim 1, wherein the target nucleic acid template is nested within a larger amplified region.

24. The method of claim 1, wherein the first-stage amplification reaction comprises site-specific primers such that the first-stage amplification reaction is selective for a particular site of interest, and wherein only if that site or region exists in the sample will rapid amplification of the template proceed at the second-stage amplification reaction.

* * * * *